(12) United States Patent
Kominami et al.

(10) Patent No.: US 8,187,873 B2
(45) Date of Patent: May 29, 2012

(54) MONOCLONAL ANTIBODY TO SOLUBLE LOX-1

(75) Inventors: Goro Kominami, Osaka (JP); Masahiro Nakamura, Settsu (JP); Noriaki Kume, Kyoto (JP); Hideki Ohta, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 554 days.

(21) Appl. No.: 12/375,210

(22) PCT Filed: Jul. 27, 2007

(86) PCT No.: PCT/JP2007/064750
§ 371 (c)(1),
(2), (4) Date: Feb. 17, 2009

(87) PCT Pub. No.: WO2008/013257
PCT Pub. Date: Jan. 31, 2008

(65) Prior Publication Data
US 2009/0203039 A1  Aug. 13, 2009

(30) Foreign Application Priority Data
Jul. 28, 2006  (JP) ............................... 2006-207054

(51) Int. Cl.
*C12N 5/07* (2010.01)
*C07K 16/00* (2006.01)
(52) U.S. Cl. ..................................... 435/326; 530/388.1
(58) Field of Classification Search .................. None
See application file for complete search history.

(56) References Cited

U.S. PATENT DOCUMENTS
2008/0241134 A1* 10/2008 Kobayashi et al. ......... 424/133.1

FOREIGN PATENT DOCUMENTS
| JP | 09-098787 | 4/1997 |
| JP | 2000-109435 | 4/2000 |
| JP | 2002-510710 | 4/2002 |
| JP | 2005-272383 | 10/2005 |

OTHER PUBLICATIONS

Kita et al, Report on Shared Research Supported by the Health and Labour Sciences Research Grants, "Significance of Measuring the Blood Concentration of Soluble LOX-1 in Ischemic Heart Disease" Mar. 2006, pp. 17-19.
The 31$^{st}$ Japan Atherosclerosis Society Meeting, Medical Tribune, vol. 32, No. 31 Aug. 5, 1999, p. 6.
Sawamura et al, An Endothelial Receptor for Oxidized Low-Density Lipoprotein, Nature, vol. 386, Mar. 6, 1997, pp. 73-77.
Murase et al, Identification of Soluble Forms of Lectin-Like Oxidized LDL Receptor-1, Arterioscler. Thromb. Vasc. Biol., 20(3) Mar. 2000, pp. 715-720.
Hayashida et al, Serum Soluble Lectin-Like Oxidized Low-Density Lipoprotein Receptor-1 Levels Are Elevated in Acute Coronary Syndrome, Circulation, 112(6), Aug. 9, 2005, pp. 812-818.
International Search Report for PCT/JP07/64750, dated Oct. 9, 2007.
Kataoka, H. et al., Expression of Lectinlike Oxidized Low-Density Lipoprotein Receptor-1 in Human Atherosclerotic Lesions, Circulation, vol. 9, pp. 3110-3117 (1999).

* cited by examiner

*Primary Examiner* — Michael Pak
(74) *Attorney, Agent, or Firm* — Roylance, Abrams, Berdo & Goodman, L.L.P.

(57) ABSTRACT

It is intended to provide a monoclonal antibody that specifically recognizes human soluble LOX-1, particularly a monoclonal antibody with a dissociation constant (Kd) for human soluble LOX-1 of $1 \times 10^{-9}$ (M) or less. The antibody can be produced from a hybridoma prepared by a method including the following steps of: (1) immunizing a non-human animal with a prokaryotic cell-derived human LOX-1 extracellular domain; (2) collecting antibody-producing cells from the animal; (3) fusing the antibody-producing cells with myeloma cells; (4) selecting hybridomas that produce a monoclonal antibody reacting with the human LOX-1 extracellular domain from the fused cells obtained in the above step; and (5) selecting a hybridoma that produces a monoclonal antibody reacting with a eukaryotic cell-derived human LOX-1 extracellular domain from the selected hybridomas.

4 Claims, 7 Drawing Sheets

MONOCLONAL ANTIBODY TO SOLUBLE LOX-1

TECHNICAL FIELD

This invention relates to monoclonal antibodies binding with specific affinity to a soluble molecule (hereafter called "soluble LOX-1") produced by cleavage of part of lectin-like oxidized low density lipoprotein receptor-1 (hereafter called "LOX-1") which is a receptor for oxidized low-specific gravity lipoproteins (Oxidized LDL), as well as a hybridoma producing these antibodies. Furthermore, this invention relates to the application of these monoclonal antibodies.

BACKGROUND TECHNOLOGY

The sequence of conditions from unstable angina to acute myocardial infarction, to sudden coronary death combined with these is inclusively referred to as Acute Coronary Syndrome (ACS). Each of these occurs when plaques generated due to arteriosclerosis of the coronary arteries supplying nutrients to the myocardium collapse and as a result of thromboses being attached thereon, coronary artery stenosis and blockage occur. Although in modern society the increase in acute coronary syndrome has been plodding along, because most of these are sudden occurrences with no forewarning, sudden death where lifesaving is impossible is a common experience. In addition, even in cases where [the patient] is quickly accepted into a hospital, emergency heart surgery, emergency percutaneous coronary angioplasty (PCI), etc., are often necessary for lifesaving, and the burdens on the medical economy are incalculable.

It has become apparent in recent years that the onset of acute coronary syndrome is caused by the formation of occlusive thromboses continually generated either by the disintegration or erosion of atheromatous arteriosclerosis plaques (non-patent reference 1). Although it has been shown that inflammatory reactions and oxidation stresses within the vascular walls carry an important role in the collapse and erosion of plaques, even among these, increased protease activity and functional impairment of the vascular walls centering on and apotosis (cell death) brought about by LDL (low-specific gravity lipoproteins) which have received the oxidation changes are known the be major factors. LOX-1 (lectin-like oxidized low density lipoprotein receptor-1) is defined as the receptor protein for oxidized LDL (non-patent reference 2).

Although the LOX-1 is normally expressed by cellular-surfaces as a membrane protein in living bodies, it is known for becoming free in the blood as a form of soluble LOX-1 after cleaved at the extracellular domains adjoining the transmembrane part through the action of protease (non-patent reference 3). In addition, because there is a marked rise in blood concentrations of this soluble LOX-1 in the acute phase of acute coronary syndrome, its possibility as a primary diagnostic marker for acute coronary syndrome has been reported (non-patent reference 4).

Therefore, it is said that acute coronary syndrome (ACS) could be prevented beforehand if the volume of soluble LOX-1 present in the blood could be accurately quantitated at an early stage. On the other hand, even though there are reports of antibodies for LOX-1, these are all general writings, and there are currently no reports on immunochemical assay systems such as ELISA, etc., for said purpose, or on high-affinity monoclonal antibodies
(Patent Documentation 1-3.)

[Non-patent Reference 1] Medical Tribune, 1999, Vol. 32, No. 31, p 6.

[Non-patent Reference 2] Nature, 1997, Vol. 386, p 73-77.

[Non-patent Reference 3] Arterioscler. Thromb. Vasc. Biol. 2000, 20 (3), p 715-720

[Non-patent Reference 4] Circulation, 2005, 112 (6), p 812-818

[Patent Reference 1] Laid-open Patent Disclosure No. H9-98787

[Patent Reference 2] Laid-open Patent Disclosure No. 2000-109435.

[Patent Reference 3] Patent Disclosure 2002-510710

DISCLOSURE OF INVENTION

Problem to be Solved by the Invention

The purpose of this invention is to provide monoclonal antibodies that specifically identify and bind to human soluble LOX-1, which is a soluble molecule of LOX-1, which is a soluble human oxidized LDL receptor, and specifically, monoclonal antibodies with a high affinity for human soluble LOX-1 for a dissociation constant with the human soluble LOX-1 of $1 \times 10^{-9}$ (M) or less. In addition, the purpose of this invention is to provide an application for the monoclonal antibodies, for example, immunochemical reagents (for example, specific detection reagents for human soluble LOX-1) wherein specific affinity and binding properties for soluble LOX-1 with this antibody are used, as well as specific and high-sensitivity detection mechanisms for the human soluble LOX-1 used in this reagent.

Furthermore, a purpose of this invention is to provide a diagnostic method for acute coronary syndrome as represented by myocardial infarction through the detection or quantitation of the human soluble LOX-1 present in the blood and a evaluation method for medicinal effect of medicines for acute coronary syndrome and these candidates.

It is possible to perform diagnosis for acute coronary syndrome and evaluation of medicinal effect of the test article for acute coronary syndrome simpler and faster than conventional methods through the detection or quantitation of the human soluble LOX-1 present in the blood using the above monoclonal antibodies. Therefore, the purpose of this invention is also to provide the above application of monoclonal antibodies to diagnosis of acute coronary syndrome and evaluation for medical effect.

Means of Solving the Problem

Upon those inventors performing pioneering research in order to solve the above problems, it was discovered that monoclonal antibodies produced by a hybridoma prepared as a screening marker for competitive binding of the soluble fraction of the human LOX-1 extracellular domain and the CHO cell-derived soluble LOX-1 has an extremely high affinity for human soluble LOX-1 with a dissociation constant of $1 \times 10^{-9}$ (M) or less, and furthermore, they confirmed that it was possible to detect and measure the presence of soluble LOX-1 in the blood, which reflects the condition of acute coronary syndrome, at a high sensitivity according to the Sandwich ELISA method using these monoclonal antibodies. From these findings it is our conviction that high-accuracy diagnosis of acute coronary syndrome and high-accuracy evaluation of medicinal effect of the test drug for acute coronary syndrome using a diagnostic kit using the monoclonal antibodies applied in this invention is possible.

This invention was completed based on the relevant findings, and includes the following features:

(I) Monoclonal Antibodies (I-1)

Monoclonal antibodies, a part thereof, specifically binding with human soluble LOX-1 or the marked substances for these.

(I-2) The monoclonal antibodies described in (I-1), a part thereof, characterized by a dissociation constant (Kd) with human soluble LOX-1 of $1\times10^{-9}$ (M) or less, or the marked substances of these.

(I-3) The monoclonal antibodies, parts thereof, or the marked substances of these, described of in (I-1) or (I-2) produced by hybridomas prepared by a method including the following steps of: (1) immunizing a non-human animal with a prokaryotic cell-derived human LOX-1 extracellular domain; (2) collecting antibody-producing cells from the animal; (3) fusing the antibody-producing cells with myeloma cells; (4) selecting hybridomas that produce a monoclonal antibody reacting with the human LOX-1 extracellular domain from the fused cells obtained in the above step; and (5) selecting a hybridoma that produces a monoclonal antibody reacting with a eukaryotic cell-derived human LOX-1 extracellular domain from the selected hybridomas.

(I-4) Monoclonal antibodies, parts thereof, produced by the hybridoma "Mouse-Mouse hybridoma sLOX-1 1A7" (Receipt No.: FERM. BP-10645) or "Mouse-Mouse hybridoma sLOX-1 6B11" (Receipt No.: FERM. BP-10646), specifically binding with human soluble LOX-1, or the marked substances of these.

(I-5) The monoclonal antibodies, parts thereof described in any of (I-1)-(I-4), where part of the monoclonal antibodies is a Fab' fragment of monoclonal antibodies specifically binding with human soluble LOX-1, or the marked substances of these.

(II) The Application of Monoclonal Antibodies, Part Thereof or the Marked Substances for These.

These monoclonal antibodies or parts thereof are capable of being used effectively in high-sensitivity detection of human soluble LOX-1 present in body fluids such as blood, etc., and is applicable in the diagnosis of acute coronary syndrome. Furthermore, these monoclonal antibodies or part thereof are capable of being used effectively in evaluating for medicinal effect of medicines for acute coronary syndrome or these candidates. Therefore, this invention includes the following features:

(II-1) The monoclonal antibodies, a part thereof described of in any of (I-1)~(I-5), or marked substances of these for the diagnosis of acute coronary syndrome.

(II-2) A method for the diagnosis of acute coronary syndrome including a step of measuring soluble LOX-1 in human fluid with the monoclonal antibodies, a part thereof described of in any of (I-1)~(I-5) or marked substances of these.

(II-3) The monoclonal antibodies or a part thereof described of in any of (I-1)~(I-5) or marked substances of these for the evaluation for medicinal effect of medicines for acute coronary syndrome or these candidates.

(II-4) A method for the evaluation for medicinal effect of medicines for acute coronary syndrome or these candidates including a step of measuring fluid of which human administrated of medicines for acute coronary syndrome or these candidates with the monoclonal antibodies, a part thereof described of in any of (I-1)~(I-5) or marked substances of these.

(III) The Hybridoma and the Preparation Method Thereof (III-1) A hybridoma producing the monoclonal antibodies described in (I-1)~(I-5).

(III-2) A hybridoma described in (II-1) prepared as marked substances for screening the competitive binding of the soluble fraction of the human LOX-1 extracellular domain and CHO cell-derived soluble LOX-1.

(III-3) A hybridoma described in (II-2) that is "Mouse-Mouse hybridoma sLOX-1 1A7" (Deposit No.: FERM BP-10645), or "Mouse-Mouse hybridoma sLOX-1 6B11" (Deposit No.: FERM BP-10646).

(III-4) A preparation methods for hybridomas as disclosed in (III-1) including the following steps of: (1) immunizing a non-human animal with a prokaryotic cell-derived human LOX-1 extracellular domain; (2) collecting antibody-producing cells from the animal; (3) fusing the antibody-producing cells with myeloma cells; (4) selecting hybridomas that produce a monoclonal antibody reacting with the human LOX-1 extracellular domain from the fused cells obtained in the above step; and (5) selecting a hybridoma that produces a monoclonal antibody reacting with a eukaryotic cell-derived human LOX-1 extracellular domain from the selected hybridomas.

(III-5) A hybridoma prepared by the method described in (III-4).

(III-6) A hybridoma described in any of (III-1)~(III-3), prepared by the method described in (III-4).

(IV) A Reagent Kit for the Detection of Human Soluble LOX-1 and Applications Thereof (IV-1) A reagent kit for human soluble LOX-1 testing including the monoclonal antibodies, a part thereof described in any of (I-1)~(I-5), or marked substances of these, as specific binding reagents or specific detection reagents for human soluble LOX-1.

(IV-2) A reagent kit described in (IV-1) which is used as an acute coronary syndrome diagnostic kit.

Furthermore, this reagent kit can also be said to be an "Acute coronary syndrome diagnostic kit including the monoclonal antibodies, a part thereof described in any of (I-1)~(I-5), or marked substances of these", (V) Specific Detection Method for Human Soluble LOX-1

(V-1) A specific detection method for human soluble LOX-1 with a process using the monoclonal antibodies of a part thereof described in any of (I-1)~(I-5), or marked substances of these as a specific binding reagent or a specific detection reagent for human soluble LOX-1.

It becomes possible to diagnose the presence of a condition of acute coronary syndrome, and the degree thereof, in a test subject from the increase in the volume of soluble LOX-1 in the blood, which is related to the condition of acute coronary syndrome, by use of this detection method.

Advantages of the Invention

Because the monoclonal antibodies of this invention specifically recognize human soluble LOX-1, and bind with a high affinity, they are useful in specific detection and specific binding with this human soluble LOX 1. According to the monoclonal antibodies of this invention, a part thereof, or marked substances thereof (or a human soluble LOX-1 detection reagent including any of these) as well as the specific detection method for human specific LOX-1 wherein these are used, it is possible to immunochemically check for the distribution and presence of soluble LOX-1 expression in living tissues or living samples, and it becomes possible to give a more detailed description of the physiological action and significance of soluble LOX-1.

In addition, the monoclonal antibodies of this invention, or part thereof, or marker (or human soluble LOX-1 detection reagent including any of these), as well as the specific detection method for human soluble LOX-1 using these, are useful in the immunochemical or immunohistological diagnosis of the various diseases and conditions generated in relation to the expression of LOX-1 (hyperactive expression, expression failure/reduction). Examples of such diseases and conditions are, arteriosclerosis accompanying the hyperactive expression of LOX-1 (or caused by the hyperactive expression), as well as for example, cardiovascular disease (ischemic heart disease, heart failure) in more advanced conditions.

In particular, it is possible to keep the blood concentration of human soluble LOX-1 with a quantitative limit of approximately 0.1 ng/mL per 1 mL of human blood serum by 2-site sandwich ELISA in which two types of monoclonal antibodies of this invention are combined as shown in the working examples. This corresponds to a measurement sensitivity of about 10 times that of conventional measurement methods.

[Preferred Embodiment of the Invention]

1. Monoclonal Antibodies and Manufacturing Method Thereof

The following describes in detail the monoclonal antibodies of this invention and the manufacturing thereof by clarifying the meanings of various terms used in this invention.

The "LOX-1" in this invention is a receptor for oxidized LDL (Oxidized Low-specific Gravity Lipoprotein) derived from mammals. Although humans, cows, goats, rabbits, mice, rats, hamsters, and marmots, etc, are available mammals, oxidized LDL receptors (oxidized low density lipoprotein receptors of humans, cows, rabbits, rats, or mice) described in the existing reports are preferred (Nature, Vol. 386, p 73-77, 1997: Shishitsu Seikagaku Kenkyu, Vol. 39, p. 83-84, 1997; Patent Disclosure Report No. H9-98787; GenBank Accession No. BAA81912; Biochem. J., Vol. 330 (Pt3), p. 1417-1422, 1998). Specifically, LOX-1 with the amino acid sequence described in amino acid sequence 1 are available.

The LOX-1 is a type II membrane protein of about 50 kDa with sugar chains added, and is composed of four domains from the N terminal, the endocellular domain, the transmembrane domain, the neck domain, and the creatine-like domain. Among these, the creatine domain operates as the recognition site for oxidized LDL. (Tatsuya Sawamura, Rinsho Kensa (Clinical Testing) vol. 445, No. 3, p 297). In the case of human LOX-1 (sequence number 1), the amino acid 1-36 region corresponds to the endocellular region, the amino acid 37-57 region corresponds to the transmembrane region and the amino acid 58-273 region corresponds to the extracellular domain.

In this invention, the "LOX-1 Extracellular Domain" means all or part of the "extracellular domain" in the entire structure of said LOX-1. Specifically, this means all or part of the partial structure (partial region) existing on the outer limits of the cellular membrane in the LOX-1 which is a transmembrane protein. Or in other words, the "LOX-1 extracellular domain" means all or part of the regions excluding the transmembrane region incorporated within the membrane as well as the region within the membrane in addition to the endocellular region existing within the cytoplasm. In the case of human LOX-1 (sequence number 1), the region 58-273 of the amino acid sequence corresponds to the extracellular domain as previously stated.

"Part of human LOX-1 Extracellular Domain" means a portion of LOX-1 extracellular domain. Specifically partial region having solubility such as "soluble LOX-1" as well as the region 58-273 (sequence number 2) of the amino acid sequence of human LOX-1 (sequence number 1) are available.

In this invention, "soluble LOX-1" means part of the LOX-1 released (secreted) in the blood after the part of the LOX-1 existing in the membrane (normally part of the extracellular, domain) is fractioned (separated)

More specifically, in the case of human LOX-1, human soluble LOX-1 means the soluble receptor which is part of the human LOX-1 extracellular domain. As an example of soluble receptor molecules corresponding to part of the human LOX-1 extracellular domain, it is possible to present a molecule formed from region 88-273 (sequence number 3) of the human LOX-1 amino acid sequence (sequence number 1), or a molecule formed from region 92-273 of the amino acids sequence (sequence number 4). In addition, the molecules corresponding to part of the human LOX-1 extracellular domain include the peptides positioned at the N terminal side of the human LOX-1 extracellular domain. Examples of these peptides are specifically, the peptides corresponding to regions 1-10 of the amino acid sequence (sequence number 5) of the soluble molecules (amino acid sequence 3), as well as the peptides of the region of amino acid sequence 1-10 (sequence number 6) of the soluble molecules (sequence number 4). Furthermore, those peptides correspond to the respective regions 88-97 and region 92-101 of the amino acid sequence of human LOX-1 (sequence number 1).

The "monoclonal antibodies" that are the subject of this invention are said monoclonal antibodies specifically binding to human soluble LOX-1. Soluble LOX-1 with amino acid sequence showing sequence numbers 3 or 4 created by the cleaving of part of the LOX-1 exists in human blood, and because its amount increases along with the progression of acute coronary disease syndrome, this soluble LOX-1 is thought of as a possible diagnostic marker reflecting the condition of arteriosclerosis and ischemic heart disease caused thereby. (Hayashida et al, Circulation, 2005, 1 12 (6), 812-8), Therefore, the "monoclonal antibodies" that are the subject of this invention are, most applicably, antibodies with a high affinity for human soluble LOX-1 with amino acid sequence showing sequence numbers 3 and 4.

The "monoclonal antibodies" of this invention with specific binding properties for human soluble LOX-1 can be prepared by existing general manufacturing methods using parts of human soluble LOX-1 extracellular domain (including natural bodies, modified bodies, synthesized substances, and supernatant of cellular cultures) as an immunogen.

Specifically, parts of human soluble LOX-1 extracellular domain are injected hypodermically, endomuscularly, venously, or into the foot pad or abdominal cavity of mammals, preferably mice, rats, hamsters, marmots, rabbits, cats, dogs, pigs, goats, sheep, donkeys, horses, or cows (including transgenic animals created in order to produce other animal-derived antibodies such as human antibody-producing transgenic mice) as an immunogen, or when necessary along with a Freund adjutant, thereby implementing an immune reaction. Normally, the immunization is performed 1~4 times every 1~21 days after initial immunization, and after about 1~10 days following the final immunization antibody producing cells can be obtained from the immunosensitized mammals. The number of times immunity is performed as well as its temporal interval can vary appropriately depending on the properties of the immunogen used.

Furthermore, the following examples can be presented as "Part of the human soluble LOX-1 extracellular domain", which is useful for reference substances, immunogen (hapten) or screening. In addition, the following examples are applicable to fraction which includes part of the human soluble LOX-1 extracellular domain in high concentration.

(a) Cells expressing human LOX-1 on the cell surface, or artificially established cell strains for expressing human LOX-1 on the cell surface, or cultured supernatant obtained by culturing genetically modified cells created using genetic recombination technology in order to express human LOX-1 on cell surfaces, or human soluble LOX-1 refined from this culture supernatant;

(b) Culture supernatant obtained by culturing genetically modified cells created using genetic recombination technology to as to express partial region of the human LOX-1 extracellular domain, or partial region of the human LOX-1 extracellular domain refined from this cultured top serum, or (c) A chemically synthesized N-side region of the human LOX-1 extracellular domain.

Specifically, soluble LOX-1 secreted in culturing fluid for cells expressing human LOX-1 can be used as the human soluble LOX-1 in (a). This is based on the soluble LOX-1 secreted in the culturing fluid for cells expressing human LOX-1 being said to be closest to natural human soluble LOX-1. This human soluble LOX-1 can be prepared by the method described in Working Example 1 (2) (Disclosed Patent Report No. 2002-17353, etc.)

In addition, part of the human LOX-1 extracellular domain (amino acid sequence 85-273 region of sequence number 1, shown as sequence number 2) can be used as a partial region of the human LOX-1 extracellular domain. This partial region can be prepared by the gene-engineered method described in Working Example 1 (1).

Furthermore, peptides with amino acid sequence described in sequence number 5 or 6 can be used as N-side region of the human LOX-1 extracellular domain in (c). These peptides need conjugation with high molecule such as bovine serum albumin (BSA) if used as hapten.

A immunogen used in this invention is preferably partial region of the human LOX-1 extracellular domain obtained from prokaryotic cell such as *e-coli*.

The preparation of the hybridoma secreting the monoclonal antibodies can be performed by the method of Koehler and Milstein et al. (Nature 1975, vol. 256, p 495~497), as well as methods based on this. In other words, hybridoma preparation is possible by the cellular fusing of antibody-producing cells included in the spleen, lymph nodes, bone marrow, or tonsils, etc., preferably spleen, obtained from immunosensitized mammals, as per the above, and myeloma cells without autonomous antibody production capability derived from mammals, preferably mice, rats, marmots, hamsters, rabbits, or humans, etc., and most preferably mice, rats or humans.

Examples of the myeloma cells used for use in cell fusion are mouse-derived myelomas P3/X63-AG8.653(653), P3/NS1/1-Ag4-1 (NS-1), P3/X63-Ag8.U1(P3U1), SP2/0-Ag14 (Sp2/O, Sp2), PAI, F0 or BW5147, rat-derived myelomas 210RCY3-Ag.2.3, and human-derived myelomas U-266AR1, GM 1500-6TG-A1-2, UC729-6, CEM-AGR, D1 R11, or CEM-T15.

Screening for the hybridoma clones producing the monoclonal antibodies is performed by culturing the hybridoma, for example in a microtiter plate, then measuring the reactivity to immunogens used in said non-human animal immune reaction (any of aforementioned (a)~(c), preferably a part of human LOX-1 extracellular domain derived from prokaryotic cell, prepared by the method disclosed in (b)) of the well culture supernatant where increase was seen by immunoassay methods such as RIA and ELISA, etc., and selecting the clones producing the monoclonal antibodies showing specific affinity for the immunogen. In this method the non-competitive ELISA method, which is said to detect antibodies in the culture supernatant binding to the solidified immunogen by a second antibody marked by an enzyme, is generally used. However, because this non-competitive method also detects non-specific binding, it is difficult to detect only specifically-binding antibodies. Furthermore, generally, when expressed by *e-coli*, the three-dimensional structure differs from that of natural items. Even with regard to parts of the human LOX-1 extracellular domain, it often becomes a precipitate material, and slurry of this precipitate and the supernatant is used as the immunogen. In this case, it is expected that many items bound to a variant protein of a precipitate differing from the both the antibody produced and natural soluble LOX-1

Then, as a result of performing the screening described in the below (1) and (2) step by step, the inventors selected hybridomas producing monoclonal antibodies capable of binding with natural human soluble LOX-1 with extremely high affinity.

(1) Bounding the antibodies in the culture supernatant of hybridoma with the solidified second antibody, add a part of human LOX-1 extracellular domain derived from prokaryotic cell, react with human soluble LOX-1 marked with biotin competitively, and select hybridomas producing the monoclonal antibodies capable of binding with part of human LOX-1 extracellular domain derived from prokaryotic cell.

(2) Bounding the antibodies in the culture supernatant of the above selected hybridoma with the solidified second antibody, add part of human LOX-1 extracellular domain derived from eukaryotic cell, react with human soluble LOX-1 marked with biotin competitively, and select hybridomas producing the monoclonal antibodies capable of binding with part of human LOX-1 extracellular domain derived from eukaryotic cell.

The manufacturing of monoclonal antibodies from hybridomas can be performed by culturing hybridomas in vitro or by culturing in ascites, etc., of mice, rats, marmots, hamsters, or humans, etc., preferably mice or rats or more preferably mice, and then isolating from the obtained culture supernatant, or mammal ascites. In the case of in vitro culturing, the hybridomas were grown, maintained, and stored matched to the characteristics of the cultured cells, the purpose of the test research, and the various conditions of the culturing method, etc., and could be performed using any nutrient culture medium induction prepared from already known nutrient culture media or already-known base culture media such as can be used to produce monoclonal antibodies in a culture supernatant.

Low-calcium culture media such as Ham' F12 culture medium, MCDB1153 culture medium, or low-calcium MEM culture media, etc., as well as high-calcium culture media such as MCDB104 culture medium, MEM culture medium, D-MEM culture medium, RPMI 1640 culture medium, ASF104 culture medium, or RD culture medium, etc. can be used as base culture media, while non-base culture media can include as needed, blood serum, hormones, cytokine, and/or various organic or inorganic substances, for example.

Separation and refinement of the monoclonal antibodies can be performed by supplying the above-mentioned culture supernatant or ascites to saturated sulfuric ammonium, ion-exchange chromatography (DEAE or DE52, etc.), or affinity column chromatography such as anti-immunoglobulin column or protein A column, etc.

The monoclonal antibodies of this invention can be monoclonal antibodies with any of the IgG (IgG1, IgG2, IgG3, IgG4), IgM, IgA (IgA1, IgA2), IgD, or IgE isotypes. IgG (IgG1, IgG2, IgG3, IgG4) are preferred, with IgG1 or IgG2 being more preferred, and IgG1 being particularly preferred.

In this invention, "part of the monoclonal antibodies" refers to part of the aforementioned monoclonal antibodies of this invention, and a region with specific binding properties for human soluble LOX-1 similar to the aforementioned monoclonal antibodies, (hereafter simply called the "antibody fragment").

Peptides, etc., containing Fab (fragment of antigen binding), F(ab')$_2$, single chain antibody (single-chain Fv; referred to as scFv below), diabody V region fragments (referred to as diabody below), disulfide-stabilized antibodies (disulfide-stabilized Fv, henceforth referred to as dsFv), dAd (single domain antibody), and CDR with specific binding properties to the aforementioned human soluble LOX-1 can be used as the antibody fragment (Expert Opinion on Therapeutic Patents. Vol. 6, No. 5, p 441~456, 1996).

Fab is an antibody fragment that is composed of about half the N terminal side of the H chain and the entire L chain, and has an antigen binding activity of a molecular weight of about 50,000. This Fab can be obtained by the papain processing of the upper peptide components of two disulfide bonds (S—S bond) cross-linking two H chains in the IgG hinge region, and the Fab used in this invention can be obtained by papain processing the aforementioned monoclonal antibodies of the invention. In addition, it is possible to manufacture Fab by inserting the DNA coding said Fab of the monoclonal antibodies of this invention into expression headers for animal cells, and expressing by the introduction of this header into animal cells.

$F(ab')_2$ is an antibody fragment that is constructed by the binding of the pepsin parts of these two Fab' regions, and has antigen binding activity of about 100,000 molecular weight. The $F(ab')_2$ is obtainable by procession of the bottom of 2 S—S bonds in the IgG hinge region with enzyme pepsin, and the $F(ab')_2$ used in this invention can be obtained by pepsin processing of the aforementioned monoclonal antibodies of this invention. In addition, $F(ab')_2$ can be manufactured by inserting DNA coding the $F(ab')_2$ of these monoclonal antibodies into the expression header for animal cells, and expressed by introduction of this header into animal cells.

Fab' is an antibody fragment with an antigen binding activity of approximately 50,000 molecular weight where the S—S bond between the hinge of said F $F(ab')_2$ is cleaved. The Fab' used in this invention can be obtained by reductant dithiothreitol processing of said $F(ab')_2$ of the monoclonal antibodies of this invention.

In addition, Fab' can be manufactured by inserting the DNA coding the Fab' of the monoclonal antibodies into the expression header of animal cells, and expressed by introducing the header into animal cells.

scFv is VH-P-VL or VL-P-VH polypeptide where a single VH and a single VL have been linked using an appropriate peptide linker (henceforth referred to as P), and is an antibody fragment with antigen activity.

The VH and VL included in the scFv used in this invention should be of the aforementioned monoclonal antibodies of this invention. The scFv used in this invention can be expressed and manufactured by obtaining the cDNA coding the VH and VL by the hybridoma producing said monoclonal antibodies of this invention, constructing a scFv expression header, and introducing it to e-coli, yeast, or animal cells.

dsFv is said to be bound by S—S binding of a polypeptide in which one respective amino acid residue in VH and VL was converted to a cysteine residue. The amino acid residue being converted to a cysteine residue is selected based on three-dimensional structure prediction of the antibody according to the method shown by Reiter et al. (Protein Engineering, 7, 697 (1994)). The VH or VL containing the dsFv used in this invention should be of the monoclonal antibodies of this invention. The dsFv used in this invention can be manufactured by obtaining cDNA coding the VH and VL from the hybridoma producing the monoclonal antibodies of this invention, constructing of a dsFv expression header through insertion into an appropriate expression header, and expressing by introduction of this expression header to e-coli, yeast, or animal cells.

The diabody is an antibody fragment formed of two scFv of identical or differing antigen binding specificity, and is an antigen fragment with bivalent antigen binding activity for the same antigen or two specific antigen binding activities for different antigens. For example, a bivalent diabody reacting specifically to the monoclonal antibodies of this invention can be manufactured by obtaining cDNA coding the VH and VL of the monoclonal antibodies of this invention constructing DNA coding scFv with 3~10 residues of peptide linkers, inserting this DNA into an expression header for animal cells, and expressing the diabody through introducing the expression header into animal cells.

Peptides containing CDR are constructed to include at least one CDR region of the VH or VL Multiple CDRs can be bound directly or by suitable peptide linkers. Peptides containing the CDR used in this invention can be manufactured by constructing the DNA coding the CDR after having obtained cDNA coding the VH or VL of the monoclonal antibodies of this invention, inserting this DNA into an expression header for animal cells, and expressing through introduction of this header into animal cells. In addition, peptides containing CDR can also be manufactured by chemical synthesis methods such as the Fmoc method (flourenyl methyl-oxycarbonyl method), the tBoc method (t-butyl oxycarbonyl method), etc.

It is preferred that $F(ab')_2$ obtained by pepsin processing of the monoclonal antibody (IgG) of this invention be used as the "monoclonal antibody part".

The dissociation constant (Kd) is used as an indicator showing affinity of monoclonal antibodies to antigens. For example, easy analysis is possible by the Scatchard method using antibodies marked with a variety of marker agents, as well as by using BiacoreX (made by Amersham Biosciences), which is an over-the-counter, measuring kit, or similar kit, according to the user's manual and experiment operation method attached with the kit, The Kd value that can be derived using these methods is expressed in units of M (Mols). The tested monoclonal antibodies show a stronger affinity the smaller as the dissociation constant (Kd).

The monoclonal antibodies or parts thereof that are subject to this invention have dissociation constant (Kd) for human soluble LOX-1 of $1\times10^{-9}$ (M) or less, preferably of $5\times10^{-10}$ (M) or less, and most preferably $2\times10^{10}$ (M) or less, and include a human monoclonal antibody or a part thereof that specifically binds with human soluble LOX-1.

Because the monoclonal antibodies or parts thereof subject to this invention have a dissociation constant of $1\times10^{-9}$ (M) or less, and have an extremely high affinity, it was assumed that high-sensitivity detection and quantitation of human-soluble LOX-1, which conventionally could not be achieved, were possible. In particular, the problem that the concentrations of soluble LOX-1 in blood serum are too low in healthy individuals to detect accurately by conventional measurement methods is solved.

On the other hand, even though monoclonal antibodies in which similar immunogens were used have been reported (WO01/64862), these are human antibodies intended for treatment, and all of the disclosed monoclonal antibodies have dissociation constants of $1\times10^{-8}$ (M) or more. At such level, it is thought that purposes as a diagnostic marker cannot be achieved from the aspect of sensitivity in cases of soluble LOX-1 measurement in healthy persons or in the chronic period because these concentrations are very low (referred to the Working Example 5 (9)).

Among the monoclonal antibodies subject to this invention, the monoclonal antibodies produced from hybridomas 6B11 or 1A7 as shown in the working examples can be considered the most suitable.

The "Dissociation Constant (Kd)" of each monoclonal antibody produced from these hybridomas 6B11 and 1A7 is shown below.

TABLE 1

| Monoclonal Antibody | Kd($\times 10^{-10}$M) |
|---|---|
| 1A7 | 5.1 |
| 6B11 | 3.4 |

These hybridomas 6B11 and 1A7 were internationally deposited at the Patent Microorganism Depository Center of the National Institute of Advanced Industrial Science and Technology (AIST) at Tsukuba Central 6, 1-1 Higashi 1-chome, Tsukuba-shi Ibaraki, Japan on Jul. 26, 2006 as "Mouse-Mouse hybridoma sLOX-1 1A7" and "Mouse-Mouse hybridoma sLOX-1 6B11". Acknowledgement Number and Deposit Number of each hybridoma is shown below.

TABLE 2

| Hybridoma Display | Acknowledgement Number | Deposit Number |
|---|---|---|
| Mouse-Mouse hybridoma sLOX-1 1A7 | FERM ABP-10645 | FERM BP-10645 |
| Mouse-Mouse hybridoma sLOX-1 6B11 | FERM ABP-10646 | FERM BP-10646 |

II. Reagent Kit for Soluble LOX-1 Detection and the Soluble LOX-1 Specific Detection Method Used Therein Said monoclonal antibodies of the invention bind specifically with human soluble LOX-1 with a high affinity.

For this reason, it is possible to both selectively and specifically detect human soluble LOX-1 through immuno assay methods by using the monoclonal antibodies of this invention, Therefore, the monoclonal antibodies of this invention can investigate the histological locality of soluble human LOX-1 and the degree of expression thereof and can be effectively used as immunological reagents (for example, reagents for immuno electrophoresis and reagents for immunoassay, etc.) for detecting and quantitating the human soluble LOX-1 present in a test sample. In other words, the aforementioned monoclonal antibodies of this invention can be effectively used as a specific binding reagent or a specific detection reagent (Immunological reagent) for human soluble LOX-1 in the detection and measure of human soluble LOX-1 using the immuno electrophoresis method or the immunoassay method. Here, direct or indirect competitive assay or non-competitive assay (for example, the sandwich method, etc.) can be presented as examples of immunoassay methods. In addition, the immuno electrophoresis method and the immunoassay method include the Western Blot method, the fluorescent antibody method, the immunoenzyme antibody method (ELISA), radioactive substance-marked immuno antibody method (RIA method), immunohistological staining methods such as the immunohistological staining method and the immunocellular staining method, etc (ABC method, CSA method, etc.), and the immuno precipitate method, etc. [Tan Kuron Kotai Jikken Manual (Monoclonal Antibody Testing Manual), Kodansha Scientific (1987); Zoku Seikagaku Jikken Kouza 5 (Continuing Lectures in Biochemistry Experiments 5); Meneki Seikagaku Kenkyu kai (Immunobiochemistry Research Society) (Tokyo Kagaku Dozin Co., Ltd. (1986), etc.)].

This invention provides a reagent kit for the specific detection or measurement of human soluble LOX-1 using the immuno electrophoresis method or the immunoassay method. This invention is characterized by being a reagent kit for detection and measurement of the presence and volume of human soluble LOX-1 in a test sample by use of the antigen-antibody reaction, and said monoclonal antibodies of this invention being included as a specific binding reagent component or specific detection reagent component for human soluble LOX-1. In addition, it is also possible to use a part with specific binding for human soluble LOX-1 (antibody fragment) instead of the monoclonal antibodies of this invention.

The monoclonal antibodies, or parts thereof (antibody fragments), of this invention can be used as is, or used in a state joined to a solid holding body as a reagent for immunoassay. Here, anything known to industry can be used as the solid holding body joined to the monoclonal antibodies or parts thereof, and examples such as glass, polystyrene, polypropylene, polyethylene, dextrane, nylon, amylase, natural/variant cellulose, polyacyl amide, agar, and magnetite are available. Furthermore, these solid holding bodies can contain wells for a reaction tray, test tubes, polystyrene tweezers, magnetic tweezers, nitrocellulose strips, membranes, latex granules, etc. Methods for binding these monoclonal antibodies or antibody fragments to the solid holding body are also commonly known, and these commonly known methods can also be applied to this invention.

In addition, the monoclonal antibodies or antibody fragments thereof of this invention can be used as is, or used in a marked material state marked by any marked agent as an immunological reagent for immuno electrophoresis and immunoassay. For marked agents useable this invention, enzymes widely known in the industry (for example alkaline phosphatase (ALP, peroxidase (HRP), etc.), radioactive isotopes (for example, $^{125}$I, $^{3}$H, $^{14}$C, etc.), fluorescent compounds (for example, flouricene isothionate (FITC), tetra methyl rhodamine iso-thio cyanate (RITC), etc.), luminescent chemical compounds, as well as bioluminescent chemical compounds, etc., have been widely presented as binding marker agents for monoclonal antibodies. Furthermore, enzyme immunoassay (EIA), enzyme immunometricassay (ELISA), radio immunoassay (RIA), fluorescent immunoassay, and luminous immunoassay, etc., have been named as immunoassay methods where these are used as maker agents.

Immunoassay methods (EIA, ELISA) using enzymes as marker agents are preferred; specifically, the ELISA method using alkaline phosphatase (ALP) as the enzyme and chemiluminescent substrate APS-5 as the coloration substrate for detection, and the ELISA method using peroxidase (HRP) as the enzyme and tetramethylbendizine color developer as the coloration substrate for detection, can be used.

A suitable reagent kit for soluble LOX-1 detection provided by this invention is a reagent kit for sandwich ELISA using two monoclonal antibodies specifically binding to human soluble LOX-1. This reagent kit contains at least monoclonal antibodies or fragment thereof, of this invention fixed within a solid holding body, monoclonal antibodies, or fragment thereof of the invention marked with said marker agent, and a substrate coloring, fluorescing, or luminescing, in reaction to this marker agent. In this case, it is preferable that said enzyme, particularly alkaline phosphatase (ALP) can be used as the marking agent, and APS-5 be used as the substrate. Detection of human soluble LOX-1 at a higher sensitivity is possible by this sandwich ELISA.

Furthermore, these marker methods by marking agents, and decorating methods through indirect marking, as well as these detection methods, etc., can be performed according to the respective publicly known methods ("Tan Kuron Koutai" (Monoclonal Antibodies) Auth. Tetsuo Iwasaki, et al, Kodansha Scientific, 1984; "Koso Meneki Sokuteiho" (Enzyme Immunoassay Methods) Vol. 2, Auth. EiJi Ishikawa, et al, Igaku Shyoin, 1982) etc,).

Suitable reaction fluids, dilution fluids, cleaning fluids, human soluble LOX-1 standard fluids, transfer solutions, phoresis solutions, reaction stopping fluids, antibody detection reagents, marker activity measurement reagents, dye liquids, reaction plates, nitrocellulose filters, polyaclyl amide gels, etc can be included in the reagent kit of this invention. Furthermore, a second antibody binding to the monoclonal antibodies of the invention, for example anti-IgG antibody and protein A, etc., marked by a radioactive substance and enzyme, etc., call be used here as an antibody detection reagent.

By using an aforementioned reagent that includes the monoclonal antibodies, antibody fragments, or marked substances of these of the invention as binding or detection reagents, it is possible to detect and measure human soluble LOX-1 easily, specifically and with high sensitivity, according to the general immune electrophoresis method and immunoassay method.

Therefore, this invention provides a specific measurement method for human soluble LOX-1 further characterized by said monoclonal antibodies, antibody fragments, and or marked substances of these of this invention as a specific binding reagent or specific detection reagent for human soluble LOX-1.

The measurement method of this invention requires the use of said monoclonal antibodies, antibody fragments, or marked substance of these of this invention as a specific binding reagent or specific detection reagent for human soluble LOX-1, and outside of this, there are no particular restrictions for other basic operations, etc., and customary methods in normal immune electrophoresis methods or immunoassay methods can be broadly adopted. Therefore, there are no particular restrictions on the antigen-antibody reaction using the monoclonal antibodies, antibody fragments, or marked substance of these, of the invention, as well as the reaction conditions of the antigen-antibody conjugate and antibody detection reagent, and normal immunoreaction conditions are adopted. The temperature conditions are normally 45° C. or less, preferably around 4~40° C., and most preferably around 25-40° C., and a pH of around 5~9, and a placement time of around 0.5~40 hours, preferably around 1-20 hours, or an incubation method can be used.

The suitable soluble LOX-1 measurement method provided by this invention is a sandwich ELISA method using two monoclonal antibodies specifically binding with human soluble LOX-1. (2-site sandwich ELISA method).

This method binds a test sample or a human soluble LOX-1 standard fluid (antigen) to a solid holding body (solidified antibody) where the monoclonal antibodies of this invention or fragments thereof that specifically bind to human soluble LOX-1 have been solidified and then reacts the monoclonal antibodies or fragments thereof this invention marked with a marker agent (marked antibodies), forming a sandwich-type composite body of the solid-phased antibody-antigen (human soluble LOX-1)-marked antibody, and performed detection or measurement of the composite body thus formed based in the luminosity due to the reaction of this marker agent with the substrate.

The monoclonal antibodies, fragments thereof and marked substances the thereof this invention specifically recognize human soluble LOX-1 and bond with it with a high affinity, therefore, human soluble LOX-1 measurement methods using said reagent kit including these antibodies are useful in the immunochemical and immunohistological diagnosis of various diseases accompanied by an increase in human soluble LOX-1 expression (or caused by an increase in human soluble LOX-1 expression) in addition to being used in the specific detection of human soluble LOX-1 in test samples (for example, blood, urine, etc.) and various tissues, as well as the distribution measurement of tissues expressing human soluble LOX-1 thereby, and the refinement of human soluble LOX-1 using affinity.

As stated in the section on prior art, LOX-1 functions as an oxidized LDL receptor, and the accumulation within the cholesterol ester cells due to intake via the oxidized LDL receptor (LOX-1) in macrophages accumulated in the vascular endothelium is known to occupy an important role in the formation of plaques in arteriosclerosis lesions. In addition, it has been shown that expression of LOX-1 is actually amplified in the vascular endothelial cells covering the initial arteriosclerosis lesions and the endothelial smooth muscle cells and macrophages of advanced arteriosclerosis plaques. In this way oxidized LDL is taken in via the oxidized LDL receptors (LOX-1), and not only are the cells of the vascular endothelium functionally impaired, but it is also tied to the functional impairment of the vascular smooth muscle cell, and foam cell conversion of macrophages, and is deeply related to the progress of atheromatous arteriosclerosis.

Furthermore, the LOX-1 or a part thereof is fractured at a location adjoining the membrane of the extracellular domain, and is shown to exist as a soluble molecule (soluble LOX-1) in the blood. Therefore, the blood concentration of soluble LOX-1 has attached attention as a diagnostic marker reflecting the degree of LOX-1 expression in cells in vivo, or in other words, the condition of acute coronary syndrome, and early diagnosis of acute coronary syndrome is thought to be possible by measurement of this (Medical tribune, 1999, Vol. 32, No. 31, p 6; Circulation. 2005, 1 12 (6), p 812-818).

Therefore, it is possible to diagnose the degree of risk for acute coronary syndrome in a test subject by measuring the human soluble LOX-1 in the subject's blood by the human soluble LOX-1 measurement method using a reagent kit containing the monoclonal antibodies, antibody fragments thereof; or marked substances thereof of said invention. In particular, diagnosis for a risk of recurrence of acute coronary syndrome is also effective (WO2007/072896).

As disclosed above, the blood concentration of human soluble LOX-1 is used as biomarker reflecting the conditions of acute coronary syndrome and therefore it is possible to evaluate the medical effect of the test drug for acute coronary syndrome with the indication of the concentration. Specifically, according to the method for measurement of human soluble LOX-1 with the reagent kit of this invention containing monoclonal antibodies, a part thereof, or marked substances of these, for example, in clinical trial for acute coronary syndrome, effect of the test drug in the subject can be evaluated easily, by measuring human soluble LOX-1 in subject's blood. Furthermore, according to the said method for measuring human soluble LOX-1, the medical effect of the test drug in the subject of acute coronary syndrome can be evaluated easily, by measuring human soluble LOX-1 in subject's blood.

WORKING EXAMPLES

The following describes proposed working examples of this invention in detail. However, the invention is not limited to this.

Working Example 1

Preparation of Reference Materials (1) Human LOX-1 Extracellular Domain and (2) CHO Cell-Derived Soluble LOX-1 were Prepared as Shown Below as Reference Material (1) LOX-1 Extracellular Domain Proteins A sequence coding part of the human 1 LOX-1 extracellular domain (sequence number 2) is incorporated to a pQE vector (Qiagen), a plasmid (pQE-hLOX-1) is formed, and introduced to e-coli (high-speed conversion e-coli DH5a Made by Nippon Gene, Inc.)

This e-coli was cultured for one night in 50 ml of LB (Luria-Bertani) culture medium containing 100 µg/mL ampicillin sodium, and 25 µg/mL sulfuric acid kanamycin, creating a starter, then after transferring this to IL of culture medium, it was cultured for 4 hours after adding 0.5 mol/L IPTG (Isopropyl β-D-Thiogalactoside).

The culture medium was centrifuged (8,000 $min^{-1}$, 10 minutes), and the enriched e-coli was slurried with 0.5mL of protease inhibitor cocktail (Made by Sigma), and 10 ml of a buffering solution containing 2.0 mg of lyzozyme (0.05M Tris hydrochloride buffering solution, pH 8.0 containing 1 mM EDTA), and placed under ice for 1 hour. Next, it was broken by ultrasonic processing (10 times in 1 minute), and the precipitate collected by centrifuging (9000 $min^{-1}$, 15 minutes). This insoluble fraction can be is dissolved in 8 mL of buffering solution B (0.01 M Tris hydrochloride buffering solution containing 8M urea, $0.1M\ NaH_2PO_4 2H_2O$, pH 8.0), and this is mixed for 1 hour at room temperature after adding 8 mL Ni-NTA agarose gel (Made by Qiagen). Next, the gel is moved to an empty column (1.1 id×13 cm), and after being fully washed with buffering fluid B containing 20 mmol/L imidazole, the LOX-1 extracellular domain proteins (sLOX-1-D) are leached with buffering solution B containing 50 nmol/L imidazole. This protein leaching fraction is dialyzed to 0.05 mol/L phosphate buffering solution (pH 9.0). Protein refolding is performed by gradually thinning the urea concentration added during dialysis at 4, 2, 1, and 0 mol/L.

At least 90% was precipitated by the dialysis, and the soluble fraction of the human LOX-1 extracellular domain (hereafter called "sLOX-1-D") finally obtained was 2.4 mg/15 mL. Upon checking the sLOX-1-D obtained by SDS-PAGE, there was about 1 band, and were confirmed that it was largely uniform sLOX-1-D.

(2) CHO Cell-Derived Soluble LOX-1

The sLOX-1 secreted in the culture fluid for human LOX-1 expressing CHO cells is thought to be closest to natural human soluble LOX-1. Here, pVP22/myc-his-LOX-1 was created by incorporating cDNA coding human LOX-1 into a pVP22/myc-his header (made by Invitrogen), and this was transfected to CHO cells, creating stable cells (expressing human LOX-1 (with C-myc-His tags)). These CHO cells expressing LOX-1 (with C-myc-His tags) were cultured in a culturing flask with 20 mL of culturing fluid (Ham's F-12 culture medium containing 10 vol % FCS (Fetal Calf Serum) and 0.04 g/dL G-418) (37° C., 5% $CO_2$), and subculturing was performed from these cultured cells according to the following method.

First, the culture medium in the culture flask was exchanged every 3~4 days, and Tripsin-EDTA processing performed when the cell were in a confluent state, and subculturing was performed after moving the collected cells to multiple culturing flasks. In addition, part of the cells were stored frozen, and were used by others for extended cultures. For extended cultures, roughly $5 \times 10^6$ cells were placed in a three-level culturing flask (500 $cm^2$, 150 ml, culturing fluid), at 37° C. for 4~6 days, find then after further-culturing for-two days after changing to a serum-free culturing fluid, the culture supernatant was then passed thorough an ultrafiltration membrane (0.22 µm filler), and put in frozen storage after adding 0.33 mL of a 10× concentration protease inhibitor cocktail.

This LOX-1 (with C-myc-His tag)-expressing CHO cell culture supernatant was collected, and affinity refined using an Ni-NTA agarose (Qiagen) column after ammonium sulfate precipitation, dialysis, and concentration. And during leaching from the Ni-NTA agarose column it was washed by finely changing the imidazole concentration at 5, 10, 20, 50, and 100 nmol/L, and the target proteins (CHO cell-derived sLOX-1) was elution sampled using 250 mmol/L of imidazole.

Working Example 2

The TR-FIA Method, as Well as the Measurement of the Antibody Titer and Affinity Using this The TR-FIA (time-resolved fluoroimmunoassay) method has been constructed as an antibody screening method. The principle of this method is to add the test sample to a second antibody solid phased plate, and bind a biotin-marked antigen to it (biotin-marked sLOX-1-D), creating a composite body, then the composite material created (second antibody sLOX-1 antibody—biotin-marked sLOX-1-D) is marked with europium (Eu) marked avidin (or Eu marked streptoavidin), and detected by the time-resolved fluorescence method. (See FIG. 1)

The reference material prepared in Working Example 1 or 2 (sLOX-1-D or CHO cell-derived sLOX-1) is added to the reaction system, and completed with the biotin-marked sLOX-1-D, making it possible to measure the affinity for the human soluble LOX-1 in the test antibody sample according to the impairment of binding of the test antibody sample to the biotin-marked sLOX-1-D.

(1) Biotin Conversion of sLOX-1-D (Preparation of Biotin-Marked sLOX-1-D)

The human LOX-1 extracellular domain protein (sLOX-1-D) prepared in Working Example 1 (1) was biotin converted using a biotin conversion reagent (sulfo-NHS-LC-biotin, made by Pierce). In other words, the following method was performed according to the manual.

(i) 0.06 mg ($3 \times 10^{-9}$ mol) sLOX-1-D is dissolved in 0.25 mL of reaction buffer (0.1 mol/L phosphate buffer, pH7.4), to which is added 0.025 mL of reaction buffer in which 0.025 mg ($4.5 \times 10^{-8}$ mol) of sulfo-NHS-LC-biotin (made by Pierce) was dissolved is added.

(ii) Reaction is performed by agitating for 2 hours at room temperature.

(iii) After reacting, the objective material (biotin-marked sLOX-1-D) is obtained by gel filtering (PD-10, Made by Amersham), and concentrated.

(2) Preparation of Second Antibody Solidified Plate

The IgG fraction (15.8 mg/mL) obtained by refining from goat anti-mouse IgG serum (Sheba Goat) with a MAPS-II kit (made by BioRad), is used as the second antibody. When using this IgG fraction, 10 µg/mL was prepared using a solidified buffer (0.05 mol/L Tris Buffer containing (0.05 g/mL sodium nitrate, pH 7.8), and 100 μL was pipetted each time into each well of a microtiter plate (maxi soap fluoro, Nunc). After setting the at least one night at room temperature, it was washed two times with a blocking buffer (a solution of 20 g/dl sucrose, and blockase (4 g per package, Snow Brand Milk Products with 100 mL of purified water and 100 mL of solidification buffer), it was then set for at least five hours after adding another 200 mL of the blocking buffer. The blocking buffer was aspirated, and after drying the plate at room temperature under reduced temperature, treated as a second antibody solidified dry plate (4° C. storage).

(3) Antibody Volume (Antibody Titer) Measurement Method

After washing the second antibody solidified plate twice with the washing fluid (physiological saline liquid containing 0.01 g/dL Tween 20 and 0.05 g/dL sodium nitrate), 50 μL dilution fluid for the test antibody sample and 100 μL marked antigen mix fluid (biotin-marked sLOX-1-D) and Eu-marked streptoavisin racemic) were added, and incubated for 16 hours at 4° C., and washed three times. Next 150 μL of enhancement reagent (1 L of 19.3 g Potassium hydrogen phthalate, 6.0 g acetate, 19.3 mg TOPO (tri-n-octylphosphine oxide), 4.59 mg NFA 2-napthoyltrifluoroacctone), and 1.0 g Triton X-100 in purified water), and the temporal dissociation fluorescence intensity of the Europium (Eu) solidified in the solid phase by a multi-label counter (1420 Arbo SX, Made by Wallach). Thus, the fluorescence intensity can derive the antibody titer of the test antibody sample from the dilution multiple of the test antibody to which a 100,000 count is applied.

Furthermore, 0.05 mol/L Tris buffer containing 0.05 g/dL BSA, 0.5 g/dL sodium nitrate, 0.98 mg/dL DTPA, 0.1 g Tween 80, and 0.9 g/dL sodium chloride can be used as the assay buffer used in preparation, etc. of the reagents of this measurement.

(4) Evaluation Method for Affinity of Antibody to Human Soluble LOX-1 (Inhibition Curve)

After adding 50 μL of dilution fluid for the test antibody sample, 50 μL of reference material solution for human soluble LOX-1 (sLOX-1-D or CHO cell expressed LOX-1), and 50 μL of marked antibody mix fluid (biotin-marked sLOX-1-D to and Eu-marked streptoavicin racemic) to the well of the second antibody solid phased plate prepared in (2), it is incubated for one night at 4° C., and washed three times.

Next, 150 μL of enhancement reagent is added, and the time-resolved fluorescence intensity of the Europium (Eu) fixed in the solid phase is measured by a multi-label counter (1420 Rabo SX, Made by Wallach). The concentration of the reference material supplied is gradually changed, and the binding between the test antibody sample and the biotin-marked sLOX-1-D is measured, and an inhibition curve created according to the concentration of the reference material. The affinity of the test antibody for the human soluble LOX-1 (dissociation constant, Kd) can be derived through Scatchard analysis of the inhibition curve data.

Working Example 3

Manufacture of Monoclonal Antibodies (1) Immunogen

The sLOX-1-D (slurry containing precipitate) prepared in Working Example 1 (1) and a peptide showing sequence numbers 5 and 6 positioned at an N terminal side of the human LOX-1 extracellular domain (Peptide1, Peptide2) were treated as a hapten. This is the reason why it was difficult to obtain soluble LOX-1 requirement for immunogen. Because CHO cell-derived soluble LOX-1 content in culture supernatant was much lower than *e-coli*-derived one, and culture supernatant contained many impure substances. A conjugate of the said hapten and bovine serum albumin (BSA, made by Sigma) was used as an immunogen.

Cys was introduced to the C terminal of each peptide for binding with the cross-linking reagent. A maleimide group was introduced to the BSA by using a cross-linking reagent N-(ε-Maleimidocaproyloxy) sulfosuccinimide ester (sulfo-EMCS, made by Pierce), and a hapten-BSA conjugate was obtained by reacting this with said peptide fragments containing SH groups. In other words, 27 mg of BSA ($4 \times 10$ mol) was dissolved in 1 mL of reaction buffer (0.05 mol/1 phosphate buffer, pH7.0), and 0.2 mL of reaction buffer in which 8.2 mg of sulfo-EMCS ($2 \times 10^{-5}$ mol) had been dissolved was added to this. This was reacted by agitating for 90 minutes at room temperature. After reacting, the maleimide-converted BSA was separated by performing gel filtering using a gel filter column (PD-10, made by Amersham) for the entire reaction fluid.

Peptide 1 showing sequence number 5 dissolved in 0.5 mL of reaction buffer (however Cys is introduced at the C terminal, 8.68 mg, $6.8 \times 10^{-6}$ mol) was added to 2 mL (1/2 of total volume) of maleimide group introduced BSA solution, and after having agitated for 1.5 hours at room temperature, was reacted overnight at 4° C. After dialysis with purified water, it was freeze-dried (peptide 1-BSA).

In addition, the same reaction using 2 mL maleimide-introduced BSA solution was performed for 8.33 mg ($6.6 \times 10^{-6}$ mol) of peptide 2 shown as sequence number 6 (with Cys) (Peptide 2-BSA).

(2) Immunization

A/J mice (6~8 weeks old, female, 10~20 g (body weight) supplied from Japan SRC) were used as immune animals. Using 20 A/J mice, they were divided into five groups, [Group 1-1 (No. 1101~1104), Group 2-1 (No. 2101~2104), Group 3-1 (No. 3101~3104), Group 4-1 (No. 4101-4104), and group 5-1 (No. 5101~5104)].

The immunogens (sLOX-1-ID, Peptide 1-BSA, and Peptide 2-BSA) were dissolved in physiologic saline and emulsified by adding an equal amount of Freund's Complete Adjuvant (Difco). Approximately 100 μg/100 μL of this emulsion was administered four times every three week intervals into the abdomen of each mouse.

TABLE 3

| Group | Immunogen | System (Mouse No.) | Direct Amount | Number of Immunizations (Interval) |
|---|---|---|---|---|
| 1-1 | sLOX-1-D | A/J (1101-1104) | Approx. 100 μg | 4 × (3 weeks) |
| 2-1 | Peptide 1-BSA | A/J (2101-2104) | Approx. 100 μg | 4 × (3 weeks) |
| 3-1 | Peptide 2-BSA | A/J (3101-3104) | Approx. 100 μg | 4 × (3 weeks) |
| 4-1 | Peptide 1-BSA | A/J (4101-4104) | Approx. 100 μg | 4 × (3 weeks) |
| 5-1 | sLOX-1-D | A/J (5101-5104) | Approx. 100 μg | 4 × (3 weeks) |

The antibody titers of each antiserum were checked by performing the TR-FIA method described in Working Example 2 with the antiserum extracted after having reacted 3-4 times treated as the test antibody samples. Table 4 shows the antibody titers for the antiserum obtained from the mice of Group 1-1 (No. 1011~1104), Group 2-1 (No. 2101~2104) and Group 3-1 (No. 3101~3104).

TABLE 4

| Mouse No. | Antigen | System | Antibody Titer (1/V) | | |
|---|---|---|---|---|---|
| | | | 2× Immunizations | 3× Immunizations | 4× Immunizations |
| 1101 | sLOX-1-D | A/J | >100000 | >200000 | — |
| 1102 | sLOX-1-D | A/J | >100000 | 100000 | — |
| 1103 | sLOX-1-D | A/J | >100000 | 200000 | — |
| 1104 | sLOX-1-D | A/J | >100000 | 200000 | — |
| 2101 | Peptide 1-BSA | A/J | 10000 | 20000 | — |
| 2102 | Peptide 1-BSA | A/J | 20000 | 30000 | 50000 |
| 2103 | Peptide 1-BSA | A/J | 2000 | 2000 | 2000 |
| 2104 | Peptide 1-BSA | A/J | 2000 | 20000 | 5000 |
| 3101 | Peptide 2-BSA | A/J | 30000 | 80000 | 200 |
| 3102 | Peptide 2-BSA | A/J | 2000 | 2000 | 500 |
| 3103 | Peptide 2-BSA | A/J | 70000 | 80000 | 30000 |
| 3104 | Peptide 2-BSA | A/J | 3000 | 5000 | 10000 |

Titer (1/V): dilution at 100000 cps

It was understood from these results, that the antibody titers of the antiserum obtained by immunization with sLOX-1-D (dilution multiple with the fluorescence intensity of 100,000 cps) were each in excess of 100000, and reached a plateau at 2~3 immunizations. In addition, it was determined from the antibody titers that any mouse splenic cells can be used in cell fusion.

Furthermore, we selected mice according to the result by the following step. Specifically, at first we examined affinity for sLOX-1-D which was used as antigen with the antiserum extracted after reacting three times as the test antibody samples by the TR-FIA method described in Working Example 2 (4). Subsequently we examined affinity for CHO cell-derived sLOX-1 from the antiserum of which affinity for sLOX-1-D was high. Inhibition curve about the mice of Group 1-1 is shown in FIG. 2. The 50% inhibition concentration with immunogenic sLOX-1-D was low (2~3 ng per well) and the value was similar, but about CHO cell-derived sLOX-1, though there was a difference by a mouse, any mice showed inhibition. In addition, the mouse antiserum which immunized the BSA conjugate with peptide 2 hapten reacted with peptide 2 highly, but did not show inhibition with CHO cell-derived sLOX-1. Therefore, we did not perform cell fusion about the mice which immunized peptide 2 hapten.

(3) Cell Fusion

According to the manner disclosed above, we collected the splenic cells from mice (No. 1103, No. 2101, No. 4013, and No. 5101) which produced an antiserum with the highest affinity for both sLOX-1-D and CHO cell-expressed sLOX-1 and cell fusion with myeloma cells was performed. P2U1 cells were selected for the myeloma cells (In company line of P3-X63.Ag8.U1 cells). Before use, a subculture was performed for 7~10 days using the myeloma subculture culture medium (RPMI-HBEPES: RPMI 1640 450 mL with 5 mL of 1 mol/L HEPES (pH 6.8), 10 mL OPK solution (oxalacetate 7.5 mg/mL, pyruvic acid 7.5 mg/mt, kanamycin 5 mg/mL) as well as 50 mL FBS (Fetal Bovine Serum) added) after thawing the myeloma cells stored in liquid nitrogen.

Three days before the cell fusion, the mouse spleens with the additional immunizations were extracted under ether anesthesia, and after washing with RPMI-HEPES (225 mL RPMI 1640 and 2.5 mL 1 mol/L Hepes (pH 6.8)), splenic cell suspension was prepared by performing processing on a mesh.

Approximately $1 \times 10^8$ cells of these spleen cells and $2 \times 10^7$ cells of the P3U1 myeloma cells were mixed, and after centrifugal separation and supernatant removal, 800 µl of 50 g/dL polyethylene glycol 4000 (PEG4000) (for gas chromatography, Merck) was added for one minute while shaking with the temperature maintained at 37° C., and further agitated for 1.5 minutes. Then 1 mL of the RPMI-HEPES was repeatedly dripped twice within 1 minute while agitating, and then 1 mL of RPMI-HEPES was dripped twice within 30 seconds while agitating. Next, 6 mL of RPMI-HEPES was added in 2 minutes while agitating, and finally 12 mL HEPES-RPMI was added.

The cells slurried in the RPMI-HEPES were centrifuged, and after removal of all the supernatant, these were slurried with 170 mL of HAT culture medium (a culture medium containing 350 mL of RPMI 1640, 50 mL of NCTC109 (GIBCO), 10 mL OPK solution, 5 mL NEAA (non-essential amino acids, GIBCO), 5 mL 1 mol/L HEPES (pH 6.8), 5 mL HAT (hypoxanthinine, aminoplatin, thymidine), 100 mL FCS, and 10 vol % BM-condemned H1 (Roche Applied Sciences)), and dispensed into approximately 9 sheets of 96-well micro plates (878 Well) for culturing ($1.1 \times 10^5$ cells/0.19 mL/well), and cultured within a 5% carbon dioxide gas incubator at 37° C. Table 5 shows the detailed conditions of each cell fusion.

TABLE 5

| | Cell Fusion Conditions | | |
|---|---|---|---|
| Mouse No. | PEG4000 mL | Number of Splenic Cells ($\times 10^8$) | Number of P3U1 Cells ($\times 10^8$) |
| 1103 | 0.8 | 1.0 | 0.2 |
| 2101 | 0.5 | 0.57 | 0.11 |
| 4103 | 0.8 | 0.68 | 0.16 |
| 5101 | 0.8 | 0.84 | 0.17 |

Colonies of several~10 colonies per well were seen at a fusion efficiency of about 100% as a result of cell fusion using PEG4000.

(4) Selection of Fused Cells due to the HAT Culture Medium

On the fifth day of culturing of the fused cells, 0.1 mL of HAT culture medium heated to 37° C. was added to each well. Using a phase differential microscope, the growth of the hybridomas was observed each day, and once the hybridomas had propagated to 1~5% of the entire well, 0.1 mL of the culture supernatant of each well was sampled. The TR-FIA method was performed as described in Working Example 2, with this as the test antibody sample, and those with high antibody titers and also strong affinity and cell growth were selected and used in the cloning below.

(5) Cloning (Dilution Method)

The hybridomas of the wells to be cloned were drawn off with a Pasteur pipette, and transferred and expanded in a 24-hole culturing plate. A part was calculated and geometrically diluted (8 stages) with HT culture medium (350 ml RPMI 1640, 50 mL NCTC109, 10 ml. OPK solution, 5 mL NEAA, 5 mL 1 mol/L HEPES (pH 6.8), 5 mL HT (hypoxyxanthine, thymidine), 100 mL FBS, and 10 vol % BM-Condemned H1) so that it reaches approximately 50 cell/mL. This 0.2 mL (cell count 0.1~10 cells/well) was pipetted into the culturing plate. 3-6 days later these were observed with a phase-differential microscope, and the cell count of each well checked. If proliferation was such as to be hybridomas, the culture supernatant for two or less per well was treated as the test antibody sample, screening performed using the TR-FIA method, and the monoclonal well selected (primary cloning) among those with good antibody titers, affinity and proliferation. Cloning (secondary cloning) was immediately performed gain for the selected wells and target antibodies selected after screening by the TR-FIA method just as in the primary cloning. Cloning was performed again (tertiary cloning) for those that had not become monoclonal. The established clones were gradually transferred to a large culturing flask while repeating the subculturing, preparing a concentration of approximately $5~10\times10^6$ cells/mL, this was pipetted 0.5 mL at a time to serum tubes (approximately 5 tubes), and these were stored in liquid nitrogen. The culture supernatant was separated at this time, and the antibody titer checked. Furthermore, after freezing the hybridomas, culturing was again performed and the cell proliferation and antibody titers checked.

Hybridomas obtained from Mouse No. 1103 were screened on the 10th day, and a total of 11 positive wells (>100,000 cps) were detected. Among these, primary cloning was performed by the dilution method for the five wells with the best proliferation, and 10 wells thought to be largely monoclonal were obtained. Furthermore, we performed the secondary cloning, screened it on the 10th day, and obtained three wells thought to be monoclonal. All were obtained from the clones of 6B11.

In addition, hybridomas obtained from Mouse No. 5101 were screened and 48 positive wells were detected. Cloning was performed for the 9 wells among those with the strongest affinity to sLOX-1-D. Screening was performed on the 10th day after cloning and secondary cloning was performed after selecting those with good antibody titers, affinity, and closeness to the singles. As a result, a total of 8 clones were obtained (1G2, 2E4, 2E5, 2G11, 3E12, 7G1, 1B8, 1A7).

Furthermore, we performed cell fusion for A/J mouse No. 2102 after immunizing three times with a BSA conjugate treating peptide 1 as a hapten. After cloning twice, clone (5C11) was established. In the same way, we obtained clone (4D1) from Mouse No. 4103 after performing screening and cloning twice. The result of the above cloning is shown in Table 6.

TABLE 6

| Mouse No. | Immunogen | Hybridoma Positive/All Wells | Monoclonal Number after Two Screenings (Clone Number) |
|---|---|---|---|
| 1103 | sLOX-1-D | 11/784 | 6B11 |
| 2101 | Peptide 1-BSA | 2/803 | 5C11 |
| 4103 | Peptide 1-BSA | 121/1144 | 4D1 |
| 5101 | sLOX-1-D | 48/580 | 1G2, 2E4, 2E5, 2G11, 3E12, 7G1, 1B8, 1A7 |

(6) Monoclonal Antibody Sampling (Culture Supernatant and Ascites)

Among the hybridomas prepared in (5), eleven types of hybridomas (1 G2, 2E4, 2E5, 2G1 1. 3E12, 7G1, 1B8, 1A7, 6B11, 5C11, 4D1) prepared treating the LOX-1 extracellular domain proteins (sLOX-1-D) or the B SA conjugate of the N-terminal peptide of the LOX-1 extracellular domain (Peptide 1) as antigens, were cultured in quantity, and monoclonal antibodies were extracted by switching to a serum free culture medium and collecting the culture supernatant thereof.

In addition, among the aforementioned hybridomas, the hybridomas (1G2, 2G11, 6B1 1, as well as 1A7) prepared with the LOX-1 extracellular domain protein (sLOX-1-D) as the immunogen, and the hybridomas (5C11, 4D1) prepared with Peptide1 as hapten, were abdominally inoculated at approximately $2~3\times10^{-6}$ cells into mice (Balb/c and Balb/c nu (nude mice) treated beforehand with 1 mL pristane. Furthermore, the hybridomas were thawed from a frozen state in liquid nitrogen, and abdominally administered to the mice after expansion culturing for 7~10 days. The mice were observed, and mice with swollen abdomens (8~17 days after administration) were killed under ether anesthesia, and the ascites within the abdomen thereafter extracted. 1.2~4.9 mL of ascites were obtained from each mouse inoculated with each hybridoma, and the antibody titers were measured (Table 7).

TABLE 7

| Clone No. | Immunogen | Mouse Breed | Antibody titer | Volume of Ascites per Mouse (mL) |
|---|---|---|---|---|
| 6B11 | LOX-1-D | Balb/c nu | ++ | 4.7 |
| 6B11 | LOX-1-D | Balb/c | ++ | 2.4 |
| 1G2 | LOX-1-D | Balb/c nu | ++ | 4.6 |
| 1G2 | LOX-1-D | Balb/c | ++ | 2.7 |
| 2G11 | LOX-1-D | Balb/c nu | ++ | 4.9 |
| 2G11 | LOX-1-D | Balb/c | ++ | 3.0 |
| 1A7 | LOX-1-D | Balb/c nu | ++ | 2.5 |
| 1A7 | LOX-1-D | Balb/c | ++ | 1.2 |
| 5C11 | Peptide 1-BSA | Balb/c nu | ++ | 2.6 |
| 5C11 | Peptide 1-BSA | Balb/c | ++ | 3.1 |
| 4D1 | Peptide 1-BSA | Balb/c nu | ++ | 3.2 |
| 4D1 | Peptide 1-BSA | Balb/c | ++ | 2.8 |

(7) Refining of Monoclonal Antibodies

Monoclonal antibodies, including the culture supernatant of the hybridomas prepared in (6) and the mouse ascites, were placed in a protein A affinity column, and refined to IgG. Specifically, approximately 1 mL of protein A solidified beads gel (approximately 1.5~2 mL as a slurry) was charged to the empty column, washed with 10 mL of binding buffer (included with the kit), creating a protein A affinity column. 0.5 ml of the hybridoma culture supernatant or the mouse ascites were mixed with 0.5~1 mL of the binding buffer and centrifugally separated, and the prepared supernatant was supplied to the protein A affinity column created above. First 20 mL of the binding buffer was flowed and the non-retained material was washed away, and then the IgG eliminated and leached using 30 mL of elution buffer (included in kit). After switching to the elution buffer, the first protein peak was extracted is the IgG solution. Because the elution buffer was acidic (pH 3.0), the leached IgG was immediately neutralized with the 1 mol/L Tris buffer (pH 9.0). The IgG obtained was stored frozen after having been dialyzed by phosphate buffered saline (PBS). As a result, 100~700 μg of IgG was obtained from part of the hybridoma culture supernatant (30~40 ml).

The isotype of the monoclonal antibodies obtained (IgG) was determined by an Mab-Based Mouse Ig Isotyping Kit (Pharmingen). As a result of the 11 types (6B11, 1G2, 2E4, 2E5, 2G11, 3E12, 7G1, 1A7, 1B8, 5C11, 4D1), nine types were IgG1, and the remainder were IgG2a and IgG2b (Table 8).

In addition, some of the dissociation constants (Kd) of these monoclonal antibodies are shown below (Table 9). Furthermore, although the various values of said Kd relate to part of the human LOX-1 extracellular domain (sequence number 2), the Kd for human soluble LOX-1 is thought to be largely identical because the difference between the human soluble LOX-1 (sequence numbers 3 and 4) and the amino acid sequence is extremely small.

TABLE 8

Properties of Monoclonal Antibodies

| Mouse No. | Immunogen | Clone No. | Affinity with sLOX-1-D | Affinity with sLOX-1 (CHO) | Proliferation | Sub-class |
|---|---|---|---|---|---|---|
| 1103 | sLOX-1-D | 6B11 | ++ | ++ | ++ | IgG1 |
| 2101 | Peptide 1-BSA | 5C11 | +++ | + | ++ | IgG1 |
| 4103 | Peptide 1-BSA | 4D1 | ++ | + | ++ | IgG2a |
| 5101 | sLOX-1-D | 1G2 | +++ | +++ | ++ | IgG1 |
| 5101 | sLOX-1-D | 2E4 | +++ | +++ | ++ | IgG1 |
| 5101 | sLOX-1-D | 2E5 | ++ | ++ | ++ | IgG1 |
| 5101 | sLOX-1-D | 2G11 | ++ | ++ | ++ | IgG1 |
| 5101 | sLOX-1-D | 3E12 | ++ | ++ | ++ | IgG1 |
| 5101 | sLOX-1-D | 7G1 | ++ | ++ | ++ | IgG1 |
| 5101 | sLOX-1-D | 1A7 | ++ | ++ | ++ | IgG1 |
| 5101 | sLOX-1-D | 1B8 | ++ | ++ | ++ | IgG2b |

TABLE 9

Dissociation Constant According to Scatchard Plot

| Hybridoma | Dissociation Constant (nM) |
|---|---|
| 6B11 | 0.34 |
| 4D11 | 0.36 |
| 2G11 | 0.16 |
| 3E12 | 1.32 |
| 7G1 | 0.12 |
| 1A7 | 0.51 |

Working Example 4

Monoclonal Antibody Combination

Among the 11 types of monoclonal antibodies (IgG, fraction of the culture supernatant) obtained in Working Example 3, 10 types were biotin marked according to the method described in Working Example 2 (1) except for antibody 1B8. The 10 biotin-linked antibodies among these and said 11 types of monoclonal antibodies were constructed into an 2-site sandwich ELISA using a solid-phased plate according to the method of Working Example 2 (2), and with regard to the antibody combination as per 110, the ELISA standard curve when assuming the sLOX-1-D and CHO cell-derived sLOX-1 to be the reference materials was investigated.

When an antibody (4D1 antibody or 5C11 antibody) prepared according to Working Example 3 with peptide 1-BSA where BSA conjugated to peptide 1 (polypeptide shown by sequence number 5 attached terminal with a cysteine for binding) treated an immunogen, is solid phased, a good response is shown even in ELISA for any combination with biotin-marked monoclonal antibodies (6B11, IG2, 2E4, 2E5, 2G11, 3E12, 7G1, 1A7, IB8) (Table 10), even though the blanks are high.

TABLE 10

Monoclonal Antibody Combinations in sLOX-1 ELISA

| | No. | 6B11 | 1A7 | 3E12 | 1G2 | 2G11 | 2E4 | 7G1 | 5C11 | 4D1 | 2E5 | 1B8 |
|---|---|---|---|---|---|---|---|---|---|---|---|---|
| Biotin-marked Antibodies | 6B11 | | ++ | − | − | − | − | − | ++ | ++ | − | − |
| | 1A7 | ++ | | − | − | − | − | − | + | ++ | − | − |
| | 3E12 | + | − | | − | − | − | − | + | + | − | − |
| | 1G2 | + | − | − | | − | − | − | ++ | ++ | + | − |
| | 2G11 | + | − | − | − | | − | − | ++ | ++ | + | − |
| | 2E4 | − | − | − | − | − | | − | ++ | ++ | − | − |
| | 7G1 | − | − | − | − | − | − | | + | + | − | − |
| | 5C11 | ++ | ++ | ++ | ++ | ++ | ++ | ++ | | − | ++ | ++ |
| | 4D1 | ++ | ++ | ++ | ++ | ++ | ++ | ++ | − | | ++ | ++ |
| | 2E5 | − | − | − | − | − | − | − | ++ | ++ | | − |
| | 1B8 | None | None | None | None | None | None | None | None | None | None | |

The 9 types of monoclonal antibodies (6B11, IG2, 2E4, 2E5, 2G11, 3E12, 7G1, 1A7, IB8) obtained after this by the immunization of sLOX-1-D, showed simultaneous binding with the antibody with regard to sLOX-1 N terminal peptides, and were recognized as having a different position from the N terminal (neoepitopes).

In the companion antibodies obtained by immunization of sLOX-1-D (6B11, IG2, 2E4, 2E5, 2G11, 3E12, 7G1, 1A7, IB8), strong responses were shown only in the 1A7 and 6B11 combinations, and implied a possibility that the recognition positions are adjacent in all the antibodies except these (Table 10).

Furthermore, the hybridomas producing the monoclonal antibodies obtained above, were internationally deposited at Patent Microorganism Depository Center of the National Institute of Advanced Industrial Science and Technology (AIST) at Tsukuba Central 6, 1-1 Higashi 1-chemo, Tsukuba-shi, Ibaraki, Japan on Jul. 26, 2006 as "Mouse-Mouse Hybridoma sLOX-1 111A7" and "Mouse-Mouse Hybridoma sLOX-1 6B11". The acknowledgement numbers of each of the hybridomas were as follows:

TABLE 11

| Hybridoma Display | Acknowledgement Number | Deposit Number |
| --- | --- | --- |
| Mouse-Mouse hybridoma sLOX-1 1A7 | FERM ABP-10645 | FERM BP-10645 |
| Mouse-Mouse hybridoma sLOX-1 6B11 | FERM ABP-10646 | FERM BP-10646 |

Working Example 5

Chemiluminescence ELISA (1) Monoclonal Antibody Fragmentation Method 50 mL of pepsin (Sigma) dilution fluid (50 μg/mL) was added to 0.25 ml of 0.02 mol/L acetate buffer solution (pH4.0) of the monoclonal antibody (IgG), and after agitation, reacted for three hours at 7° C. After completion of reaction, the F(ab')$_2$ fraction (molecular weight approximately 92,000) separated for a holding time of about 18 minutes by the gel filter HPLC system (Shimadzu LC-6A, Column: TSK-Gel G3000SWXLJ, 6.8×399 mm, Elute: 0.1 mol/L phosphate buffer containing 0.2 mol/L sodium chloride, pH 7.0, Flow speed: 0.5 mL/min, Detection: 280 nm).

After concentrating the F(ab')$_2$ fraction with a centrifugal ultra filter (YM-30, Centricon), 0.32 mg were added to 0.025 mL 0.1 mol/L 2-mercaptoethylamide added to 0.25 mL buffer A (0.1 mol/L phosphate buffer containing 5 mmol/L EDTA, pH 6.0), and reduced for 90 minutes at 37° C. After the reaction was complete, the Fab' fraction (molecular weight 46,000) was extracted for a holding time of approximately 20 minutes with a gel filter HPLC system. The separated Fab' fraction was concentrated with a centrifugal ultra filter (YM30).

(2) Antibody Marking Method with Alkali Phosphatase 1 mg of alkali phosphatase (ALP, derived from bovine small intestine, Kikkoman) was dissolved in 0.2 mL of 0.1 mol/L phosphate buffer (pH7.0), added N-(8-malemidocapryloxy)sulfosuccimide dissolved in 0.05 mL distilled water and 0.1 mg, sodium salt (sulfo-HMCS, Dojindo Laboratories) and reacted for 2 hours at room temperature. After completion of reaction, this was refined with a PD-10 column (Elute:Buffer A), and thereafter the high molecular fraction was concentrated by a centrifugal ultra filter (YM-10, Centricon), and floated as maleimide-converted ALP.

0.026 ml (0.128 mg) of the Fab' of said maleimide-converted ALP solution was added to 0.25 mL of the buffer containing 0.13 mg of the monoclonal antibody prepared in (1), and after agitating, it was reacted for 16 hours at room temperature. After the reaction was complete (holding time, approximately 15 minutes) 0.15 mL of the reaction fluid was separated and refined with a gel filter HPLC system (Elute: 0.1 mol/L phosphate buffer containing 0.2 mol/L sodium chloride, pH 7.0) treat this was treated as the ALP-marked antibody (ALP-marked Fab').

(3) The IgG fractions (1G2: 2.0 mg, 2G11: 1.9 mg, and 6B11:1.3 mg) of the three types of monoclonal antibodies (1G2, 2G11, 6B11) obtained from the optimum dosage study culture supernatant or ascites of the ALP-marked monoclonal antibodies (1G2, 2G11, 6B11) were reduced after pepsin processing according to (1) and (2) above, and reacted with the maleimide ALP, and the three types of Fab'-ALP conjugated (enzyme-marked antibodies) were separated using the gel filler HPLC. The enzyme-marked antibodies obtained were 0.41 mg, 0.42 mg, and 0.29 mg, respectively.

The evaluations of the three types of enzyme-marked antibodies obtained (1 G2, 2G11, 6B11) were investigated using three types of solid-phase antibodies (5C11, 4D1, 1A7). As a result, a good response was shown for all the enzyme-marked antibodies obtained (1G2, 2G11, 6B11) and the three types of solid-phase antibodies (5C11, 4D1, 1A7), and it was understood that all of the enzyme-marked antibodies created could be used in ELISA. Furthermore, the volume of enzyme-marked antibodies used per well was 100 μL with 170 ng/mL for 1G2, 150 ng/mL for 2G11, and 190 ng/mL for 6B11.

(4) Measurement Method for Human Serum Samples by Chemiluminescence ELISA

Using 100 μL (1 μg/100 μL) of the solidified buffer dilution fluid for monoclonal antibody IgG (IgG for 1A7), an antibody solid-phase converted dry plate was created by an operation based on the second antibody solid-phase converted dry plate creation method spoken of in Working Example 2 (2).

After washing this plate two times with the washing liquid (physiologic saline containing 0.01 g/dL Tween20 and 0.05 g/dL sodium nitrate), 100 μL of the sLOX-1-D standard solution or the CHO cell-derived sLOX-1 refined solution (add 10 μL of the sample to 100 μL of the assay buffer during human blood serum sample measurement) to each well, and set for 5 minutes. After washing three times, 100 μL of the ALP-marked antibody solution (6B11 Fab'-ALP conjugate) was added. After incubating overnight at room temperature, and washing four times, a chemiluminescence base solution (100 μL) was added to the solid phase, and the luminosity of each well immediately measured by a multi-level counter. Lumigen APS-5 (Oriental Yeast) was used as the luminescent base. Furthermore, 1A7-6B11 (solid-phase antibody-ALP-marked antibody) was used as the solid-phased antibody and ALP-marked antibody combination.

Furthermore, for the assay buffers used in the reagent preparation, etc., 0.05 mol/L Tris buffer (pH 7.4) containing 0.5 g/dL BSA, 0.05 g/dL sodium nitrate, 0.01 g/dL Tween 80, 1 mmol/L magnesium chloride, 0.1 mmol/L zinc chloride, and 0.9 g/dL sodium chloride was used.

(5) Selection of ELISA System

According to Working Example 5 (4), a chemiluminescence 2-site sandwich ELISA standard curve (0.24~250 pg/well) using LOX-1 extracellular membrane proteins as the reference material was created using plates where three types of enzyme-marked antibodies (1G2, 2G11, 6B11) and monoclonal antibodies 1A7, 5C11, and 4D1 of IgG had been solid phased (1 μg/0.1 ml). All of the combinations showed a high response, and in particular, the combinations of solid-phased antibodies and marked antibodies (Fab'-ALP conjugate) 1A7-6B11, 5C11-1G2, and 4D1-2G11 obtained high-sensitivity standard curves. Among these, the highest response was the 1A7-6B11 combination (estimated detection limit 0.24 pg/well (approximately 6 amol/well)), though the blanks were slightly high.

Even in the standard curve for chemiluminescence 2-site sandwich ELISA with CHO cell-derived sLOX-1 as the reference material, it was known that the sensitivity of 1A7-6B11 was around 100× better than 5C11-1G2 and 4D1-2G11 used with the antibody for peptide 1 solid-phased (FIG. 3).

(6) Effect of the Serum Components on ELISA

Human blood serum (pooled blood serum of five human volunteers), rabbit plasma, and. calf serum was diluted to 1/1~1/64, and 50 µL (serum volume 0.78~50 µL/well) and measured using the aforementioned three types of assay systems.

Although there was hardly any response with animal serums in the ELISA system for 1A7-6B11 (solid-phased antibody—ALP-marked antibody), a response was seen with human serum corresponding to the serum amount, and dilution linearity was seen in a range of 0.78~12.5 µL. These results show that it is possible to specifically measure the human sLOX-1 in the human serum (FIG. 4).

In addition, because it was estimated that the effect of blood serum components where the human blood serum sampling dose is 10 µL or less is extremely small, a serum sampling volume of 10 µL was assumed, and the standard solution was prepared without human serum included.

(7) Effect of Mouse, γ-Globulin on ELISA

It is known that humans carrying blood-home anti-mouse antibody (human anti-mouse antibody, HAMA) exist in a proportion that cannot be ignored, and in ELISA human blood test show an abnormally high value. This impairment can be suppressed by the addition of mouse γ-globulin (IgG) beforehand to the assay buffer, even in this ELISA. Upon checking the effect of mouse γ-globulin concentrations on the ELISA standard curve, there was hardly any of effect up to 20 µg/mL and so the addition of 10 µg/mL mouse γ-globulin to the assay buffer was decided upon. Furthermore, HAMA did not exist in the serum of the five volunteers used here. FIG. 5 shows the ELISA standard curve created by an assay buffer containing the mouse γ-globulin.

(8) Pre-Validation and Estimate of Limits of Determination

Pre-validation was performed using samples which were at a concentration of 0.100~12.8 ng/mL (1~128 pg/well) by addition of s-LOX-1-D to the volunteer serum (No. 3) wherein sLOX-1 concentration was low. As shown in Table 12, the accuracy and fidelity was good (1.7~15.7% and −10.5~+14.4%) in experiments in the range of 0.100~6.40 ng/mL. The accuracy and fidelity was also good between experiments in the same concentration range (5.3~12.3% and −8.3~+7.5%). On the other hand, the fidelity was somewhat poor at high concentrations (12.8 ng/ml), and it was thought that improvements are possible though revision of the standard curve points and the recursion calculation method. We estimated from these results that the limit of determination as about 0.1 ng/mL. An improvement in sensitivity of ×10 over the ELISA method where polyclonal antibodies are used (limit of determination: 1 ng/mL) was achieved.

The time of the first and second reactions of this ELISA (5 hours and overnight, respectively) matched the polyclonal antibody specifications, and because monoclonal antibodies were used it was possible to shorten the reaction time, and upon checking the accuracy/fidelity in the experiments with a four-hour first reaction arid 1 hour secondary reaction, problem-free results were obtained as shown in Table 13 (2.3~14.7% and 14.1~1 6.0%, respectively).

TABLE 12

|  | Measurement 1 (ng/mL) | | | | | Measurement 2 (ng/mL) | | | | | Measurement 3 (ng/mL) | | | | |
| --- | --- | --- | --- | --- | --- | --- | --- | --- | --- | --- | --- | --- | --- | --- | --- |
| Added Dose | 0.100 | 0.40 | 1.60 | 6.40 | 12.8 | 0.100 | 0.40 | 1.60 | 6.40 | 12.8 | 0.100 | 0.40 | 1.60 | 6.40 | 12.8 |
| Measured Value | 0.116 | 0.384 | 1.68 | 5.87 | 11.0 | 0.127 | 0.33 | 1.65 | 5.49 | 9.41 | 0.085 | 0.403 | 1.57 | 6.52 | 12.0 |
|  | 0.101 | 0.342 | 1.74 | 5.77 | 11.2 | 0.102 | 0.34 | 1.57 | 5.67 | 9.72 | 0.109 | 0.373 | 1.95 | 5.92 | 10.6 |
|  | 0.108 | 0.416 | 1.65 | 6.01 | 10.7 | 0.103 | 0.38 | 1.69 | 5.48 | 9.33 | 0.102 | 0.385 | 1.83 | 5.66 | 11.0 |
|  | 0.111 | 0.335 | 1.67 | 5.99 | 10.7 | 0.083 | 0.36 | 1.68 | 5.82 | 9.36 | 0.127 | 0.374 | 1.90 | 6.07 | 11.0 |
|  | 0.110 | 0.393 | 1.69 | 5.90 | 10.5 | 0.094 | 0.39 | 1.58 | 5.47 | 9.33 | 0.121 | 0.349 | 1.90 | 6.42 | 12.0 |
| Average | 0.109 | 0.374 | 1.69 | 5.91 | 10.9 | 0.102 | 0.358 | 1.63 | 5.59 | 9.4 | 0.109 | 0.377 | 1.83 | 6.12 | 11.3 |
| Standard Curve in Experiment | 0.005 | 0.035 | 0.03 | 0.10 | 0.3 | 0.016 | 0.023 | 0.06 | 0.15 | 0.2 | 0.017 | 0.020 | 0.15 | 0.36 | 0.6 |
| Accuracy/Fidelity Coefficient | 4.6 | 9.4 | 1.8 | 1.7 | 2.8 | 15.7 | 6.4 | 3.7 | 2.7 | 2.1 | 15.6 | 5.3 | 8.2 | 5.9 | 5.3 |
| Bias | 9.0 | −6.5 | 5.6 | −7.7 | −14.8 | 2.0 | −10.5 | 1.9 | −12.7 | −26.6 | 9.0 | −5.8 | 14.4 | −4.4 | −11.7 |
| Average |  |  |  |  |  |  |  |  |  |  | 0.106 | 0.370 | 1.72 | 5.87 | 10.5 |
| Standard Curve in Experiment |  |  |  |  |  |  |  |  |  |  | 0.013 | 0.026 | 0.12 | 0.31 | 0.9 |
| Accuracy/Fidelity Coefficient |  |  |  |  |  |  |  |  |  |  | 12.3 | 7.0 | 7.0 | 5.3 | 8.6 |
| Bias |  |  |  |  |  |  |  |  |  |  | 6.0 | −7.5 | 7.5 | −8.3 | −18.0 |

TABLE 13

Accuracy and Fidelity in Short-time Measurement Conditions for sLOX-1 ELISA (First Reaction Time; 4 hours, second reaction time: 1 hour)

| Added Amount | Accuracy/Fidelity in Experiment (ng/mL) | | | | |
| --- | --- | --- | --- | --- | --- |
|  | 0.100 | 0.40 | 1.60 | 6.40 | 12.8 |
| Measurement Value | 0.110 | 0.394 | 1.64 | 6.13 | 11.7 |
|  | 0.096 | 0.387 | 1.89 | 6.04 | 10.8 |
|  | 0.106 | 0.369 | 1.69 | 6.31 | 10.7 |
|  | 0.133 | 0.410 | 1.92 | 6.03 | 11.2 |
|  | 0.133 | 0.388 | 1.97 | 6.30 | 10.6 |
| Average | 0.116 | 0.39 | 1.82 | 6.16 | 11.0 |
| S.D | 0.017 | 0.015 | 0.15 | 0.14 | 0.4 |
| V.C | 14.7 | 3.8 | 8.2 | 2.3 | 3.6 |
| Bias | 16.0 | −2.5 | 13.8 | −3.8 | −14.1 |

(9) Measurement of Serum sLOX-1

Using this assay system, the sLOX-1 concentration in the blood serum obtained from five healthy volunteers (immunoreactivity with sLOX-1-D as the reference material) was measured. The sLOX-1 values of healthy human serum was 0.15-0.57 ng/mL as shown in Table 14, and measurement of sLOX-1 in healthy human serum, which could not be measured by ELISA with the conventional methods (polyclonal antibody specification ELISA), could be measured. Furthermore, no relationship with gender or age could be seen from these measurement results.

TABLE 14

Measurement Results for Healthy Human Volunteer Serum by sLOX-1 ELISA

| Serum No. | Volunteer Gender and Age | sLOX-1 ng/mL |
|---|---|---|
| No. 1 | M 40 | 0.37 |
| No. 2 | F 34 | 0.21 |
| No. 3 | M 51 | 0.15 |
| No. 4 | M 51 | 0.54 |
| No. 5 | F 26 | 0.57 |
| Average | | 0.37 |
| ±Standard Deviation | | 0.19 |
| Pool | | 0.35 |

As the mean concentration of s-LOX-1 in the healthy subject's blood was 0.35 ng/mL, the molar concentration in the serum was about $2 \times 10^{-11}$ M considering its molecular weight. And the sample was diluted 10 times before measurement, the molar concentration in the measurement was estimated about $2 \times 10^{-12}$ M. On the other hand, s LOX-1 concentration is totally estimated about $2 \times 10^{-12}$ M considering that 0.1% of high affinity antibodies such as this invention (Kd=$1 \times 10^{-10}$ M or less) bind to sLOX-1. In this way, by using the high affinity monoclonal antibody, we can measure sLOX-1 in the healthy subject's serum and make an accurate diagnosis.

[Sequence Table Free Text]

Figure 1:
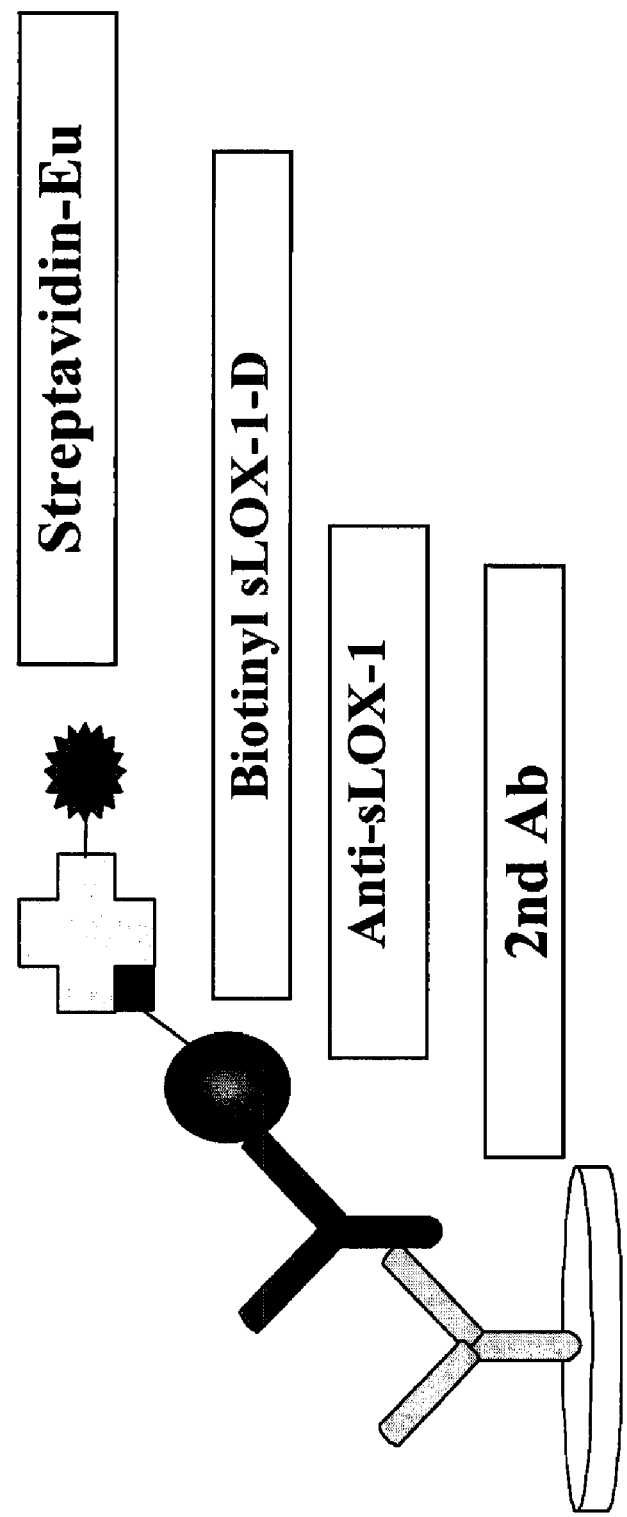
[FIG. 1] This shows a schematic diagram of the 2-site sandwich ELISA where monoclonal antibody screening of this invention was used.
Figure 2:
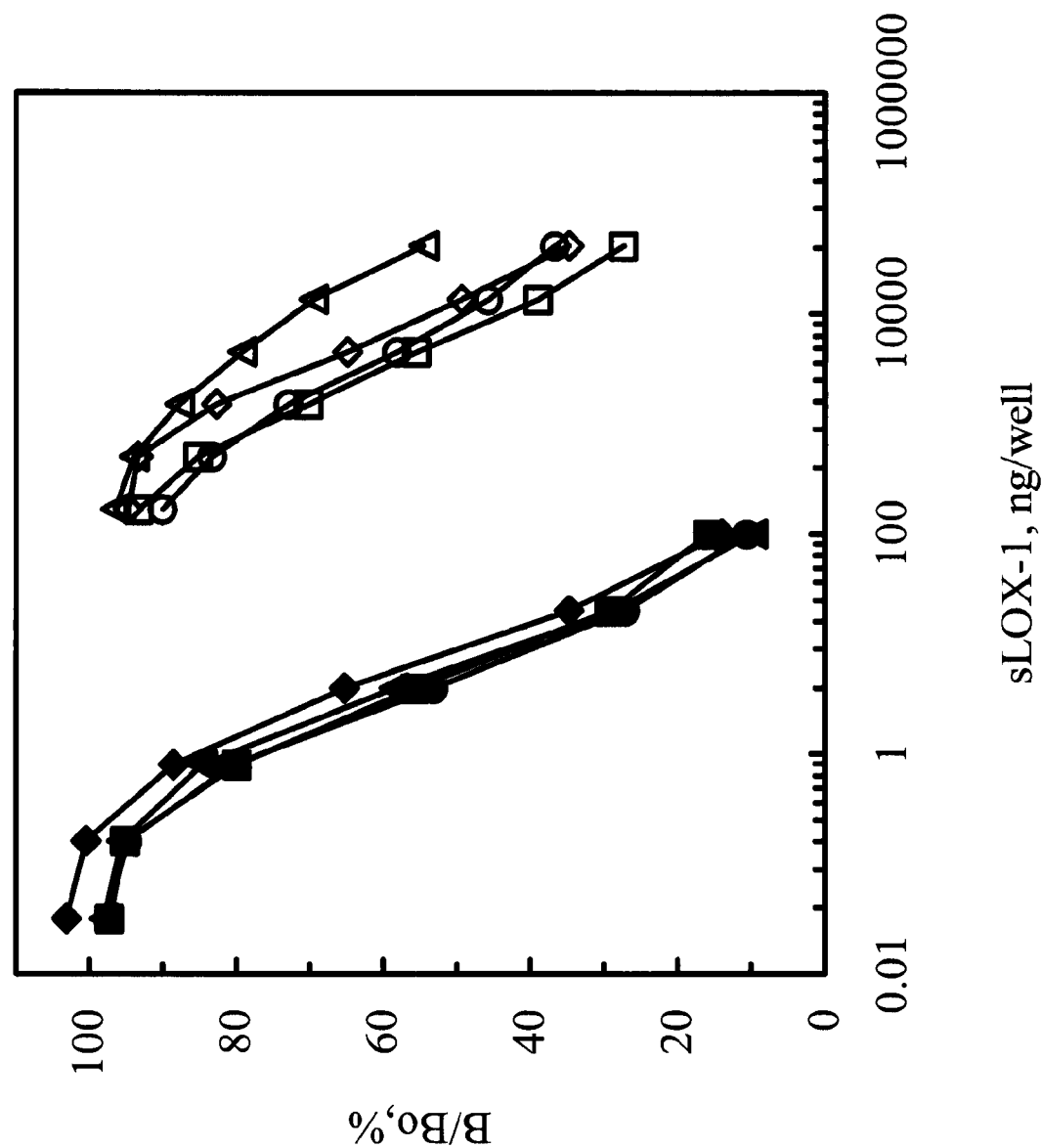
[FIG. 2] This is a graph created using antiserums for A/J mice (No. 1101 (circle mark), No. 1102 (triangle mark), No. 1103 (square mark), and No. 1104 (diamond mark)) created by sLOX-1-D immunization and with the reference material sLOX-1-D (black mark) and CHO cell-derived sLOX-1 (white mark) as the inhibition substances and the results performing TR-FIA as the inhibition curve (Working Example 3). The vertical axis shows the percentage relative to the luminosity of the zero luminosity concentration (Bo) of each concentration (B), and the horizontal axis shows the concentration of the LOX-1 extracellular domain proteins (sLOX-1-D) or the estimated concentration (ng/well) of the soluble LOX-1 (sLOX-1) from the LOX-1 expressing CHO cells.
Figure 3A:
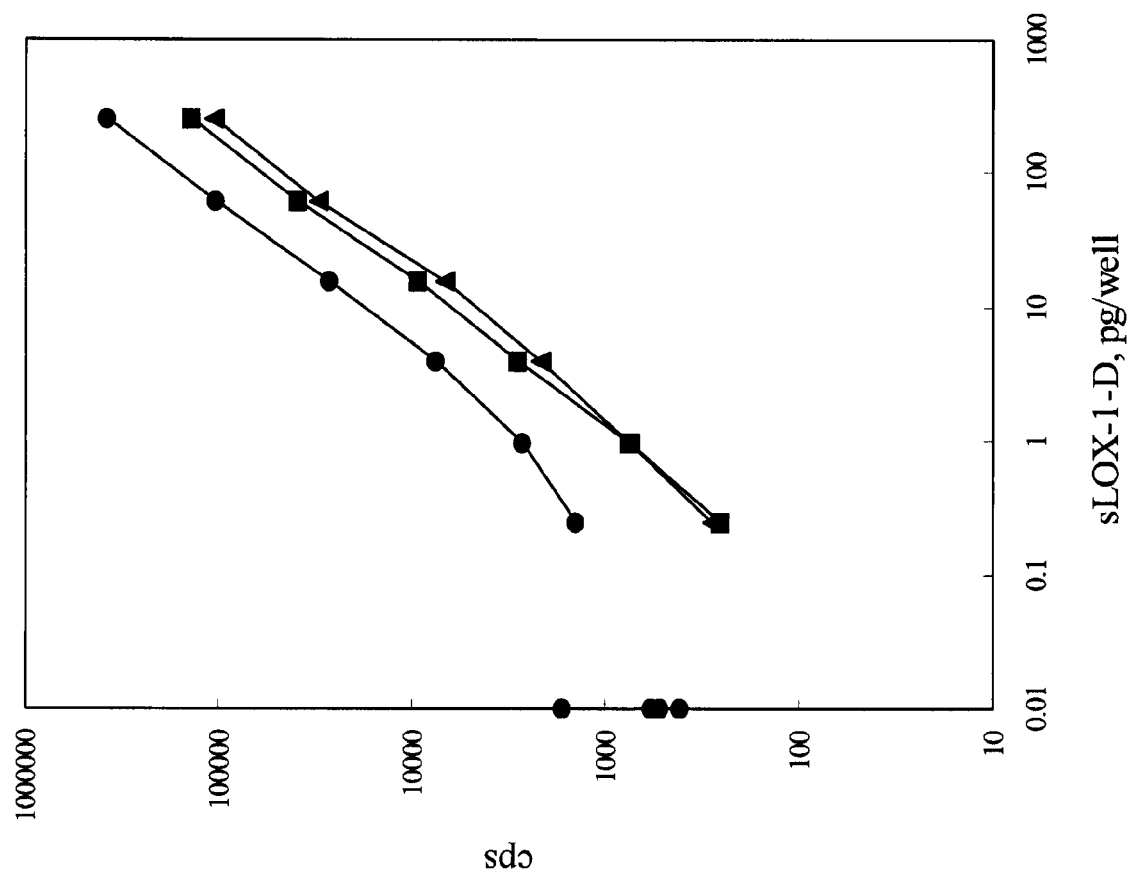
[FIG. 3] This shows the standard curve for 2-site sandwich ELISA performed using 1A7-6B11 (●), 5C11-1G2 (▲), and 4D1-2G11 (■) as the solid phased antibody-marked antibody. FIG. A shows the standard curve for ELISA performed using sLOX-1-D as the reference material, and FIG. B shows the standard curve for ELISA performed using CHO cell-derived sLOX-1 as the reference material (Working Example 5 (4)). The vertical axis shows the luminosity (cps) and the horizontal axis shows the added concentration (pg/well) of each reference material.
Figure 3B:
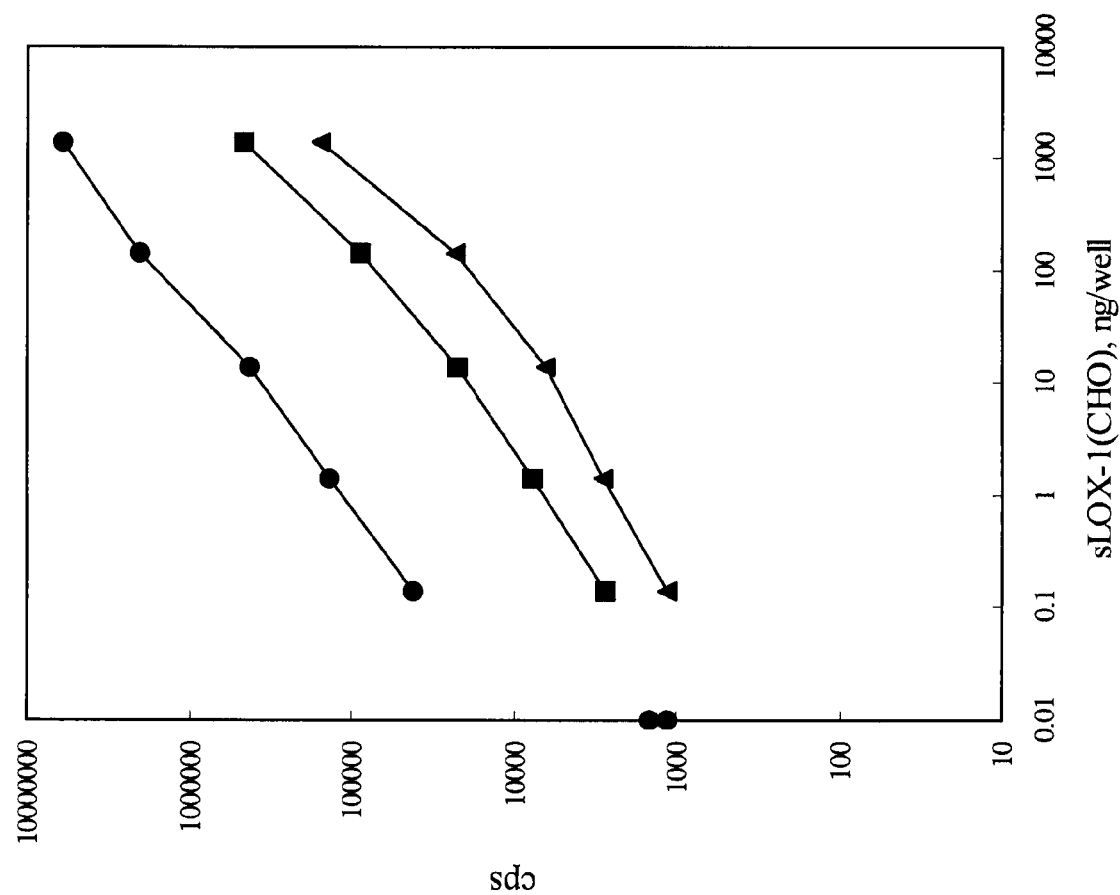
Figure 4:
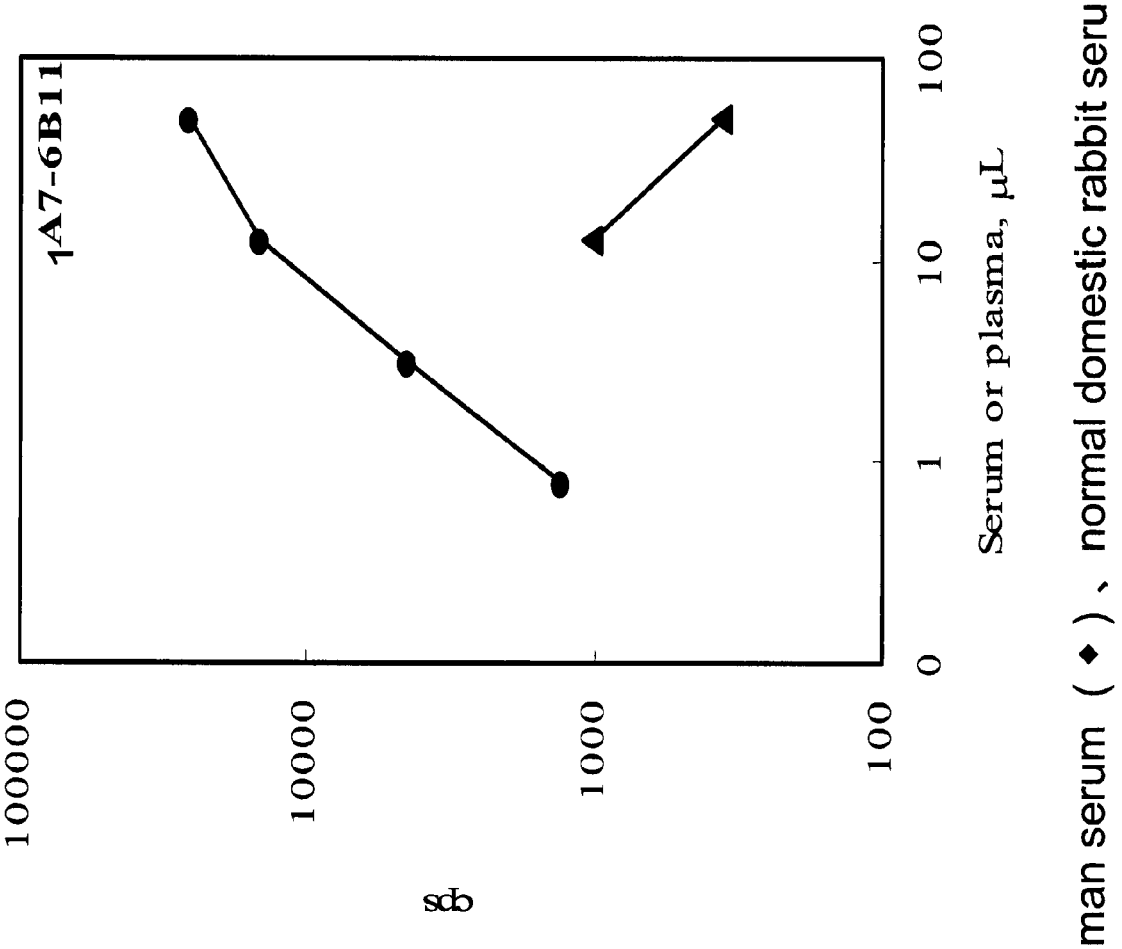
[FIG. 4] This shows the response of 2-site sandwich ELISA where 1A7-6B11 was used as the solid-phased antibody-marked antibody to each serum (human serum ♦, normal domestic rabbit serum ▲ (Working Example 5 (6)). The vertical axis shows the luminosity (cps) and the horizontal axis shows the shows the added volume (μl) of the serum.
Figure 5A:
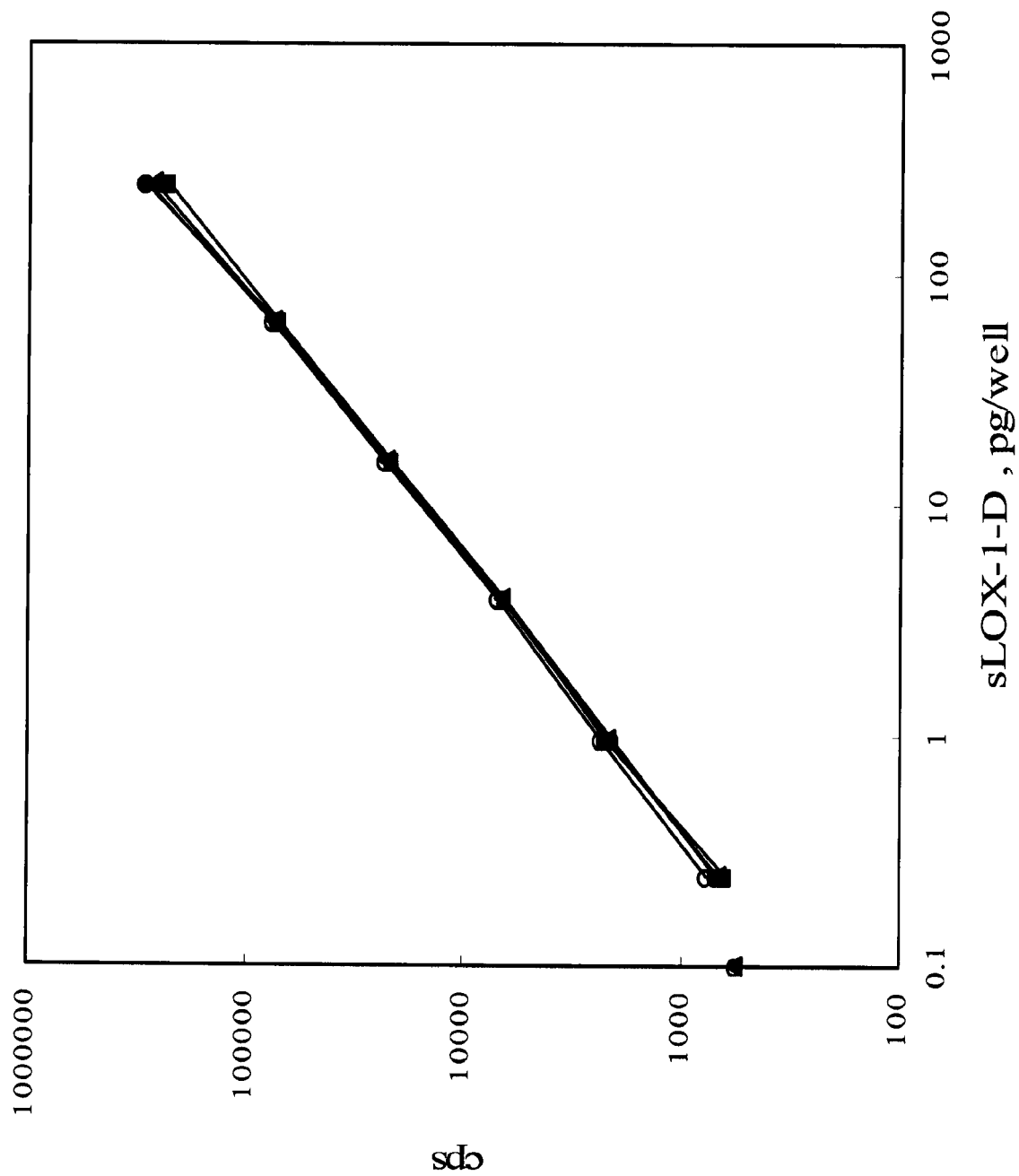
FIG. 5 shows the log-log plot, and FIG. B shows the semi-log plot. The vertical axis shows the luminosity (cps) and the horizontal axis, shows the added concentration (ps/well) of the reference material (sLOX-1-D). The added γ-globulin concentrations were 0 mg/mL (○), 5 μg/mL (●), 10 μg/mL (♦), and 20 μg/mL (■).
Figure 5B:
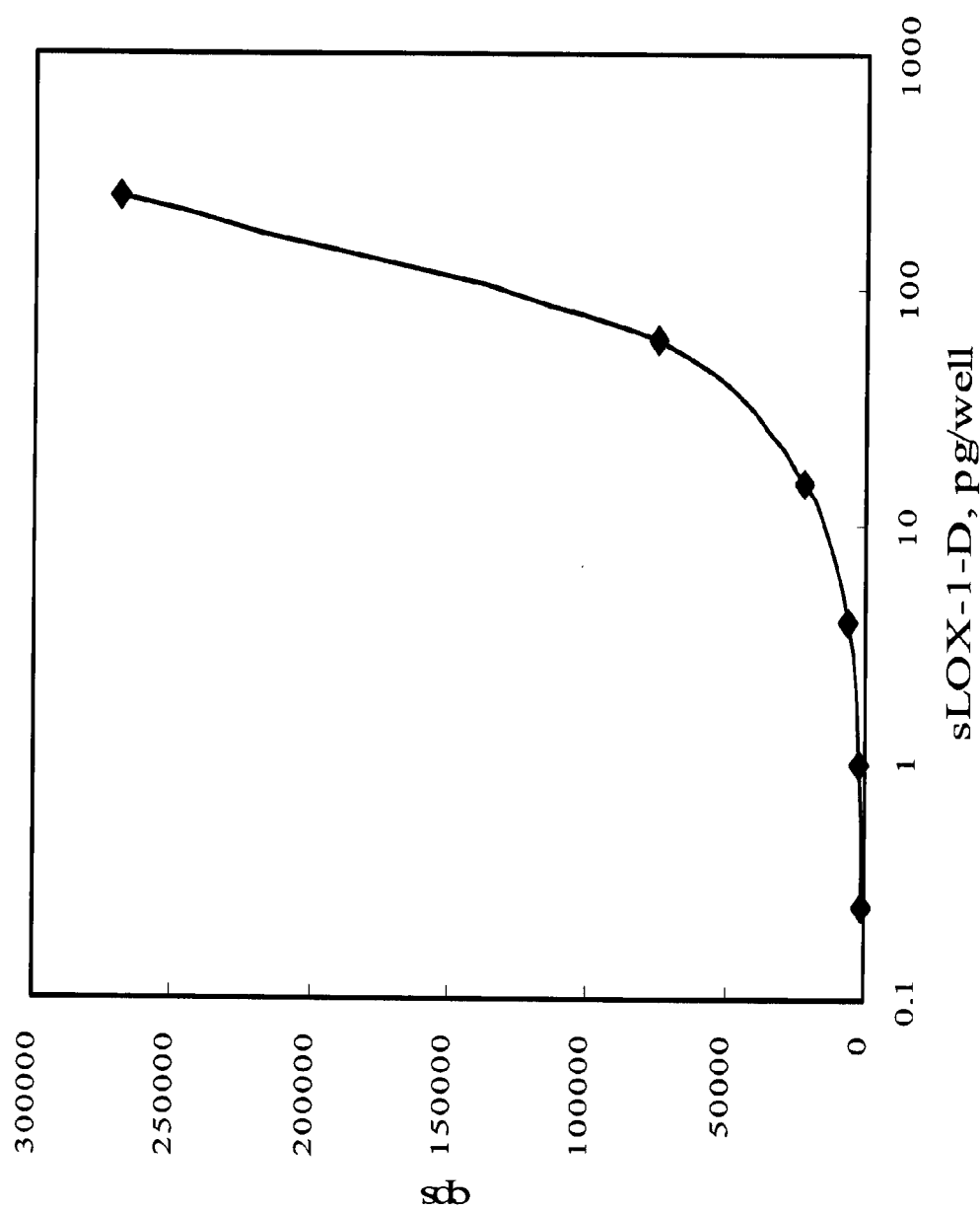

Sequence number 5 shows the amino acid sequence of the peptides corresponding to the regions 1~10 of the amino acid sequence of the soluble molecules (sequence number 3). This corresponds to regions 88~97 of the amino acid sequence of human LOX-1 (sequence number 1).

Sequence number 6 shows the amino acid sequence of the peptides corresponding to the regions 1~10 of the amino acid sequence of the soluble molecules (sequence number 4). This corresponds to regions 92~101 of the amino acid sequence of human LOX-1 (sequence number 1).

The invention claimed is:

1. Monoclonal antibodies or parts thereof that specifically bind human soluble LOX-1, characterized by a dissociation constant (Kd) with human soluble LOX-1 of $1 \times 10^{-9}$ (M) or less, wherein the monoclonal antibodies are of the IgG1 subclass and the monoclonal antibodies are produced by the hybridoma "Mouse-Mouse hybridoma sLOX-1 1A7" (Receipt No.: FERM. BP-10645) or "Mouse-Mouse hybridoma sLOX-1 6B11" (Receipt No.: FERM. BP-10646), or the marked substances of these.

2. A hybridoma producing the monoclonal antibodies as disclosed in claim 1, which is "Mouse-Mouse hybridoma sLOX-1 1A7" (Deposit No.: FERM BP-10645), or "Mouse-Mouse hybridoma sLOX-1 6B11" (Deposit No.: FERM BP-10646).

3. A reagent kit for human soluble LOX-1 detection including the monoclonal antibodies, a part thereof, or marked substances of these, as disclosed in claim 1.

4. The reagent kit as disclosed in claim 3, which is a diagnostic kit for acute coronary syndrome.

* * * * *

SEQUENCE LISTING

```
<160> NUMBER OF SEQ ID NOS: 6

<210> SEQ ID NO 1
<211> LENGTH: 273
<212> TYPE: PRT
<213> ORGANISM: Homo sapiens

<400> SEQUENCE: 1

Met Thr Phe Asp Asp Leu Lys Ile Gln Thr Val Lys Asp Gln Pro Asp
1               5                   10                  15

Glu Lys Ser Asn Gly Lys Lys Ala Lys Gly Leu Gln Phe Leu Tyr Ser
                20                  25                  30

Pro Trp Trp Cys Leu Ala Ala Ala Thr Leu Gly Val Leu Cys Leu Gly
            35                  40                  45

Leu Val Val Thr Ile Met Val Leu Gly Met Gln Leu Ser Gln Val Ser
    50                  55                  60

Asp Leu Leu Thr Gln Glu Gln Ala Asn Leu Thr His Gln Lys Lys Lys
65                  70                  75                  80

Leu Glu Gly Gln Ile Ser Ala Arg Gln Gln Ala Glu Glu Ala Ser Gln
                85                  90                  95
```

```
Glu Ser Glu Asn Glu Leu Lys Glu Met Ile Glu Thr Leu Ala Arg Lys
                100                 105                 110

Leu Asn Glu Lys Ser Lys Glu Gln Met Glu Leu His His Gln Asn Leu
            115                 120                 125

Asn Leu Gln Glu Thr Leu Lys Arg Val Ala Asn Cys Ser Ala Pro Cys
        130                 135                 140

Pro Gln Asp Trp Ile Trp His Gly Glu Asn Cys Tyr Leu Phe Ser Ser
145                 150                 155                 160

Gly Ser Phe Asn Trp Glu Lys Ser Gln Glu Lys Cys Leu Ser Leu Asp
                165                 170                 175

Ala Lys Leu Leu Lys Ile Asn Ser Thr Ala Asp Leu Asp Phe Ile Gln
            180                 185                 190

Gln Ala Ile Ser Tyr Ser Ser Phe Pro Phe Trp Met Gly Leu Ser Arg
        195                 200                 205

Arg Asn Pro Ser Tyr Pro Trp Leu Trp Glu Asp Gly Ser Pro Leu Met
210                 215                 220

Pro His Leu Phe Arg Val Arg Gly Ala Val Ser Gln Thr Tyr Pro Ser
225                 230                 235                 240

Gly Thr Cys Ala Tyr Ile Gln Arg Gly Ala Val Tyr Ala Glu Asn Cys
                245                 250                 255

Ile Leu Ala Ala Phe Ser Ile Cys Gln Lys Lys Ala Asn Leu Arg Ala
            260                 265                 270

Gln

<210> SEQ ID NO 2
<211> LENGTH: 189
<212> TYPE: PRT
<213> ORGANISM: Homo sapiens

<400> SEQUENCE: 2

Ile Ser Ala Arg Gln Gln Ala Glu Glu Ala Ser Gln Glu Ser Glu Asn
1               5                   10                  15

Glu Leu Lys Glu Met Ile Glu Thr Leu Ala Arg Lys Leu Asn Glu Lys
                20                  25                  30

Ser Lys Glu Gln Met Glu Leu His His Gln Asn Leu Asn Leu Gln Glu
            35                  40                  45

Thr Leu Lys Arg Val Ala Asn Cys Ser Ala Pro Cys Pro Gln Asp Trp
        50                  55                  60

Ile Trp His Gly Glu Asn Cys Tyr Leu Phe Ser Ser Gly Ser Phe Asn
65                  70                  75                  80

Trp Glu Lys Ser Gln Glu Lys Cys Leu Ser Leu Asp Ala Lys Leu Leu
                85                  90                  95

Lys Ile Asn Ser Thr Ala Asp Leu Asp Phe Ile Gln Gln Ala Ile Ser
            100                 105                 110

Tyr Ser Ser Phe Pro Phe Trp Met Gly Leu Ser Arg Arg Asn Pro Ser
        115                 120                 125

Tyr Pro Trp Leu Trp Glu Asp Gly Ser Pro Leu Met Pro His Leu Phe
130                 135                 140

Arg Val Arg Gly Ala Val Ser Gln Thr Tyr Pro Ser Gly Thr Cys Ala
145                 150                 155                 160

Tyr Ile Gln Arg Gly Ala Val Tyr Ala Glu Asn Cys Ile Leu Ala Ala
                165                 170                 175

Phe Ser Ile Cys Gln Lys Lys Ala Asn Leu Arg Ala Gln
            180                 185
```

```
<210> SEQ ID NO 3
<211> LENGTH: 186
<212> TYPE: PRT
<213> ORGANISM: Homo sapiens

<400> SEQUENCE: 3

Arg Gln Gln Ala Glu Ala Ser Gln Glu Ser Glu Asn Glu Leu Lys
1               5                   10                  15

Glu Met Ile Glu Thr Leu Ala Arg Lys Leu Asn Glu Lys Ser Lys Glu
            20                  25                  30

Gln Met Glu Leu His His Gln Asn Leu Asn Leu Gln Glu Thr Leu Lys
        35                  40                  45

Arg Val Ala Asn Cys Ser Ala Pro Cys Pro Gln Asp Trp Ile Trp His
    50                  55                  60

Gly Glu Asn Cys Tyr Leu Phe Ser Ser Gly Ser Phe Asn Trp Glu Lys
65                  70                  75                  80

Ser Gln Glu Lys Cys Leu Ser Leu Asp Ala Lys Leu Leu Lys Ile Asn
                85                  90                  95

Ser Thr Ala Asp Leu Asp Phe Ile Gln Gln Ala Ile Ser Tyr Ser Ser
            100                 105                 110

Phe Pro Phe Trp Met Gly Leu Ser Arg Arg Asn Pro Ser Tyr Pro Trp
        115                 120                 125

Leu Trp Glu Asp Gly Ser Pro Leu Met Pro His Leu Phe Arg Val Arg
    130                 135                 140

Gly Ala Val Ser Gln Thr Tyr Pro Ser Gly Thr Cys Ala Tyr Ile Gln
145                 150                 155                 160

Arg Gly Ala Val Tyr Ala Glu Asn Cys Ile Leu Ala Ala Phe Ser Ile
                165                 170                 175

Cys Gln Lys Lys Ala Asn Leu Arg Ala Gln
            180                 185

<210> SEQ ID NO 4
<211> LENGTH: 182
<212> TYPE: PRT
<213> ORGANISM: Homo sapiens

<400> SEQUENCE: 4

Glu Glu Ala Ser Gln Glu Ser Glu Asn Glu Leu Lys Glu Met Ile Glu
1               5                   10                  15

Thr Leu Ala Arg Lys Leu Asn Glu Lys Ser Lys Glu Gln Met Glu Leu
            20                  25                  30

His His Gln Asn Leu Asn Leu Gln Glu Thr Leu Lys Arg Val Ala Asn
        35                  40                  45

Cys Ser Ala Pro Cys Pro Gln Asp Trp Ile Trp His Gly Glu Asn Cys
    50                  55                  60

Tyr Leu Phe Ser Ser Gly Ser Phe Asn Trp Glu Lys Ser Gln Glu Lys
65                  70                  75                  80

Cys Leu Ser Leu Asp Ala Lys Leu Leu Lys Ile Asn Ser Thr Ala Asp
                85                  90                  95

Leu Asp Phe Ile Gln Gln Ala Ile Ser Tyr Ser Ser Phe Pro Phe Trp
            100                 105                 110

Met Gly Leu Ser Arg Arg Asn Pro Ser Tyr Pro Trp Leu Trp Glu Asp
        115                 120                 125

Gly Ser Pro Leu Met Pro His Leu Phe Arg Val Arg Gly Ala Val Ser
    130                 135                 140

Gln Thr Tyr Pro Ser Gly Thr Cys Ala Tyr Ile Gln Arg Gly Ala Val
145                 150                 155                 160
```

```
Tyr Ala Glu Asn Cys Ile Leu Ala Ala Phe Ser Ile Cys Gln Lys Lys
                165                 170                 175
Ala Asn Leu Arg Ala Gln
            180

<210> SEQ ID NO 5
<211> LENGTH: 10
<212> TYPE: PRT
<213> ORGANISM: Artificial Sequence
<220> FEATURE:
<223> OTHER INFORMATION: soluble peptide portion of human LOX-1 protein

<400> SEQUENCE: 5

Arg Gln Gln Ala Glu Glu Ala Ser Gln Glu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: soluble peptide portion of human LOX-1 protein

<400> SEQUENCE: 6

Glu Glu Ala Ser Gln Glu Ser Glu Asn Glu
1               5                   10
```